(12) United States Patent
Kamogawa et al.

(10) Patent No.: US 8,529,896 B2
(45) Date of Patent: Sep. 10, 2013

(54) ANTI-BST2 ANTIBODY

(75) Inventors: Yumiko Kamogawa, Tokyo (JP); Sahori Namiki, Tokyo (JP); Minkwon Cho, Tokyo (JP); Koji Ishida, Tokyo (JP)

(73) Assignees: SBI Biotech Co., Ltd., Tokyo (JP); Chugai Seiyaku Kabushiki Kaisha, Tokyo (JP)

( * ) Notice: Subject to any disclaimer, the term of this patent is extended or adjusted under 35 U.S.C. 154(b) by 245 days.

(21) Appl. No.: 12/738,285

(22) PCT Filed: Oct. 16, 2008

(86) PCT No.: PCT/JP2008/068794
§ 371 (c)(1),
(2), (4) Date: Jul. 9, 2010

(87) PCT Pub. No.: WO2009/051201
PCT Pub. Date: Apr. 23, 2009

(65) Prior Publication Data
US 2010/0278832 A1    Nov. 4, 2010

(30) Foreign Application Priority Data
Oct. 16, 2007   (JP) .................................. 2007-269470

(51) Int. Cl.
*A61K 39/395*   (2006.01)

(52) U.S. Cl.
USPC ..................................... 424/133.1; 530/387.1

(58) Field of Classification Search
None
See application file for complete search history.

(56) References Cited

U.S. PATENT DOCUMENTS

| | | | | |
|---|---|---|---|---|
| 5,914,252 | A * | 6/1999 | Hirano et al. | 435/69.5 |
| 7,592,005 | B2 * | 9/2009 | Tahara | 424/143.1 |
| 2004/0136982 | A1 * | 7/2004 | Tahara | 424/143.1 |
| 2006/0078539 | A1 | 4/2006 | Kosaka et al. | |
| 2008/0305121 | A1 | 12/2008 | Ohkawa et al. | |

FOREIGN PATENT DOCUMENTS

| | | |
|---|---|---|
| EP | 1 354 896 A1 | 10/2003 |
| EP | 1378752 A1 | 1/2004 |
| EP | 1693069 A1 | 8/2006 |
| WO | WO 98/35698 A1 | 8/1998 |
| WO | WO 99/43803 A1 | 9/1999 |
| WO | WO 02/057316 A1 | 7/2002 |
| WO | WO 02/064159 A1 | 8/2002 |
| WO | WO 02/084290 A1 | 10/2002 |
| WO | WO 2005/034994 A1 | 4/2005 |
| WO | WO 2006/008886 A1 | 1/2006 |
| WO | WO 2006/013923 A1 | 2/2006 |
| WO | WO 2006/054748 A1 | 5/2006 |
| WO | WO 2008/127261 A1 | 10/2008 |

OTHER PUBLICATIONS

Brown et al (J. Immunol. May 1996; 156(9):3285-3291.*
Vajdos et al (J. Mol. Biol. Jul. 5, 2002;320(2); 415-428).*
Goto et al. (1994) "A Novel Membrane Antigen Selectively Expressed on Terminally Differentiated Human B Cells" *Blood* 84(6):1922-1930.
Ishikawa et al. (1995) "Molecular Cloning and Chromosomal Mapping of a Bone Marrow Stromal Cell Surface Gene, BST2, That May Be Involved in Pre-B-Cell Growth" *Genomics* 26:527-534.
Kawai et al. (2006) "Antitumor activity of humanized monoclonal antibody against HM1.24 antigen in human myeloma xenograft models" *Oncology Reports* 15:361-367.
Koishihara et al. (1998) "A Humanized Anti-HM1.24 Monoclonal Antibody to a Plasma Cell-Specific Antigen for the Treatment of Multiple Myeloma" *Blood* 92(s):107a(Abstract #437, Poster Board#/Session: 437-I).
Ohtomo et al. (1999) "Molecular Cloning and Characterization of a Surface Antigen Preferentially Overexpressed on Multiple Myeloma Cells" *Biochemical and Biophysical Research Communications* 258:583-591.
Ozaki et al. (1997) "Immunotherapy of Multiple Myeloma with a Monoclonal Antibody Directed Against a Plasma Cell-Specific Antigen, HM1.24" *Blood* 90(8):3179-3186.
Jalili, A. et al. (2005) "Induction of HM1.24 peptide-specific cytotoxic T lymphocytes by using peripheral-blood stem-cell harvests in patients with multiple myeloma," Blood 106(10):3538-3545.

* cited by examiner

*Primary Examiner* — Sheela J Huff
(74) *Attorney, Agent, or Firm* — Foley & Lardner LLP; Antoinette F. Konski; Alex Y. Nie

(57) ABSTRACT

BST2 antibodies were selected by using as an indicator the binding between BST2 antibodies and various splicing variants of human BST2 antigen. As a result, the present inventors successfully obtained BST2 antibodies that specifically recognize BST2D, which has been reported to be expressed at high levels in cancer cells. The antibodies of the present invention specifically bind to cells expressing BST2D. Non-specific antibody binding to non-target tissues, which results in the decrease of antibody concentration in blood, can be prevented by using the antibodies of the present invention therapeutically. Alternatively, the present invention provides diagnostic agents comprising an antibody of the present invention, which specifically detect tissues expressing BST2D.

19 Claims, 8 Drawing Sheets

SEQUENCE LISTING

```
<160> NUMBER OF SEQ ID NOS: 37

<210> SEQ ID NO 1
<211> LENGTH: 866
<212> TYPE: DNA
<213> ORGANISM: Homo sapiens
<220> FEATURE:
<221> NAME/KEY: CDS
<222> LOCATION: (4)..(546)

<400> SEQUENCE: 1 tgg atg gca tct act tcg tat gac tat tgc aga gtg ccc atg gaa gac      48
    Met Ala Ser Thr Ser Tyr Asp Tyr Cys Arg Val Pro Met Glu Asp
    1               5                   10                  15 ggg gat aag cgc tgt aag ctt ctg ctg ggg ata gga att ctg gtg ctc      96
Gly Asp Lys Arg Cys Lys Leu Leu Leu Gly Ile Gly Ile Leu Val Leu
                20                  25                  30 ctg atc atc gtg att ctg ggg gtg ccc ttg att atc ttc acc atc aag     144
Leu Ile Ile Val Ile Leu Gly Val Pro Leu Ile Ile Phe Thr Ile Lys
            35                  40                  45 gcc aac agc gag gcc tgc cgg gac ggc ctt cgg gca gtg atg gag tgt     192
Ala Asn Ser Glu Ala Cys Arg Asp Gly Leu Arg Ala Val Met Glu Cys
        50                  55                  60 cgc aat gtc acc cat ctc ctg caa caa gag ctg acc gag gcc cag aag     240
Arg Asn Val Thr His Leu Leu Gln Gln Glu Leu Thr Glu Ala Gln Lys
    65                  70                  75 ggc ttt cag gat gtg gag gcc cag gcc gcc acc tgc aac cac act gtg     288
Gly Phe Gln Asp Val Glu Ala Gln Ala Ala Thr Cys Asn His Thr Val
80                  85                  90                  95 atg gcc cta atg gct tcc ctg gat gca gag aag gcc caa gga caa aag     336
Met Ala Leu Met Ala Ser Leu Asp Ala Glu Lys Ala Gln Gly Gln Lys
                100                 105                 110 aaa gtg gag gag ctt gag gga gag atc act aca tta aac cat aag ctt     384
Lys Val Glu Glu Leu Glu Gly Glu Ile Thr Thr Leu Asn His Lys Leu
            115                 120                 125 cag gac gcg tct gca gag gtg gag cga ctg aga aga gaa aac cag gtc     432
Gln Asp Ala Ser Ala Glu Val Glu Arg Leu Arg Arg Glu Asn Gln Val
        130                 135                 140 tta agc gtg aga atc gcg gac aag aag tac tac ccc agc tcc cag gac     480
Leu Ser Val Arg Ile Ala Asp Lys Lys Tyr Tyr Pro Ser Ser Gln Asp
    145                 150                 155 tcc agc tcc gct gcg gcg ccc cag ctg ctg att gtg ctg ctg ggc ctc     528
Ser Ser Ser Ala Ala Ala Pro Gln Leu Leu Ile Val Leu Leu Gly Leu
160                 165                 170                 175 agc gct ctg ctg cag tga gatcccagga agctggcaca tcttggaagg            576
Ser Ala Leu Leu Gln
                180
```

-continued

```
tccgtcctgc tcggctttc gcttgaacat tcccttgatc tcatcagttc tgagcgggtc    636
atggggcaac acggttagcg gggagagcac ggggtagccg agaagggcc tctggagcag     696 gtctggaggg gccatggggc agtcctgggt gtggggacac agtcgggttg acccagggct    756
gtctccctcc agagcctccc tccggacaat gagtccccc tcttgtctcc caccctgaga    816
ttgggcatgg ggtgcggtgt gggggggcatg tgctgcctgt tgttatgggt              866
```

<210> SEQ ID NO 2
<211> LENGTH: 180
<212> TYPE: PRT
<213> ORGANISM: Homo sapiens

<400> SEQUENCE: 2

```
Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Leu Leu
            20                  25                  30

Ile Ile Val Ile Leu Gly Val Pro Leu Ile Ile Phe Thr Ile Lys Ala
        35                  40                  45

Asn Ser Glu Ala Cys Arg Asp Gly Leu Arg Ala Val Met Glu Cys Arg
    50                  55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Met
                85                  90                  95

Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Arg Glu Asn Gln Val Leu
    130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Gly Leu Ser
                165                 170                 175

Ala Leu Leu Gln
            180
```

<210> SEQ ID NO 3
<211> LENGTH: 19
<212> TYPE: PRT
<213> ORGANISM: Homo sapiens

<400> SEQUENCE: 3

```
Asn Gln Val Leu Ser Val Arg Ile Ala Asp Lys Lys Tyr Tyr Pro Ser
1               5                   10                  15

Ser Gln Asp
```

<210> SEQ ID NO 4
<211> LENGTH: 6
<212> TYPE: PRT
<213> ORGANISM: Mus musculus

<400> SEQUENCE: 4

```
Ser Gly Tyr Tyr Trp Asn
1               5
```

<210> SEQ ID NO 5

```
<211> LENGTH: 17
<212> TYPE: PRT
<213> ORGANISM: Mus musculus

<400> SEQUENCE: 5

Tyr Ile Ser Tyr Asp Gly Ser Asn Asn Tyr Asn Pro Ser Leu Lys Asn
1               5                   10                  15
Arg

<210> SEQ ID NO 6
<211> LENGTH: 6
<212> TYPE: PRT
<213> ORGANISM: Mus musculus

<400> SEQUENCE: 6

Ile Leu Gly Arg Gly Tyr
1               5

<210> SEQ ID NO 7
<211> LENGTH: 15
<212> TYPE: PRT
<213> ORGANISM: Mus musculus

<400> SEQUENCE: 7

Arg Ala Ser Gln Ser Val Ser Thr Ser Ser Tyr Ser Tyr Met His
1               5                   10                  15

<210> SEQ ID NO 8
<211> LENGTH: 7
<212> TYPE: PRT
<213> ORGANISM: Mus musculus

<400> SEQUENCE: 8

Tyr Ala Ser Asn Leu Glu Ser
1               5

<210> SEQ ID NO 9
<211> LENGTH: 9
<212> TYPE: PRT
<213> ORGANISM: Mus musculus

<400> SEQUENCE: 9

Gln His Ser Trp Glu Ile Pro Tyr Thr
1               5

<210> SEQ ID NO 10
<211> LENGTH: 396
<212> TYPE: DNA
<213> ORGANISM: Mus musculus

<400> SEQUENCE: 10
atgaaagtgt tgagtctgtt gtacctgttg acagccattc ctggtatcct gtctgatgta      60
cagcttcagg agtcaggacc tggcctcgtg aaaccttctc agtctctgtc tctcacctgc     120
tctgtcactg gctactccat caccagtggt tattactgga actggatccg gcagtttcca     180
ggaaacaaac tggaatggat gggctacata agctacgacg gtagcaataa ctacaaccca     240
tctctcaaaa atcgaatctc catcactcgt gacacatcta agaaccagtt tttcctgaag     300
ttgaattctg tgactactga ggacacagct acatattact gtgcaattct gggacgcggc     360
tactggggcc aaggcaccac tctcacagtc tcctca                              396

<210> SEQ ID NO 11
<211> LENGTH: 114
```

```
<212> TYPE: PRT
<213> ORGANISM: Mus musculus

<400> SEQUENCE: 11

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Ile Leu Gly Arg Gly Tyr Trp Gly Gln Gly Thr Leu Thr Val
            100                 105                 110

Ser Ser

<210> SEQ ID NO 12
<211> LENGTH: 393
<212> TYPE: DNA
<213> ORGANISM: Mus musculus

<400> SEQUENCE: 12
atggagacag acacactcct gctatgggtg ctgctgctct gggttccagg ttccactggt     60
gacattgtgc tgacacagtc tcctgcttcc ttagctgtat ctctggggca gagggccacc    120
atctcatgca gggccagcca aagtgtcagt acatctagct atagttatat gcactggtac    180
caacagaaac caggacagcc acccaaactc ctcatcaagt atgcatccaa cctagaatct    240
ggggtccctg ccaggttcag tggcagtggg tctgggacag acttcaccct caacatccat    300
cctgtggagg aggaggatac tgcaacatat tactgtcagc acagttggga gattccgtac    360
acgttcggag gggggaccaa gctggaaata aaa                                 393

<210> SEQ ID NO 13
<211> LENGTH: 111
<212> TYPE: PRT
<213> ORGANISM: Mus musculus

<400> SEQUENCE: 13

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110
```

```
<210> SEQ ID NO 14
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 14
tccagagttc caggtcaagg tcac                                              24

<210> SEQ ID NO 15
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 15
gccagtggat agaccgatgg                                                   20

<210> SEQ ID NO 16
<211> LENGTH: 36
<212> TYPE: DNA
<213> ORGANISM: Artificial
<220> FEATURE:
<223> OTHER INFORMATION: An artificially synthesized primer sequence
<220> FEATURE:
<221> NAME/KEY: modified_base
<222> LOCATION: (24)..(25)
<223> OTHER INFORMATION: n is inosine
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: modified_base
<222> LOCATION: (29)..(30)
<223> OTHER INFORMATION: n is inosine
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (34)..(35)
<223> OTHER INFORMATION: n is inosine
<220> FEATURE:
<221> NAME/KEY: misc_feature
<222> LOCATION: (34)..(35)
<223> OTHER INFORMATION: n is a, c, g, or t

<400> SEQUENCE: 16
ggccacgcgt cgactagtac gggnngggnn gggnng                                 36

<210> SEQ ID NO 17
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 17
ggccacgcgt cgactagtac                                                   20

<210> SEQ ID NO 18
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 18
```

```
ttcactgcca tcaatcttcc actt                                              24

<210> SEQ ID NO 19
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 19
gatggataca gttggtgcag c                                                 21

<210> SEQ ID NO 20
<211> LENGTH: 480
<212> TYPE: DNA
<213> ORGANISM: Homo sapiens
<220> FEATURE:
<221> NAME/KEY: CDS
<222> LOCATION: (4)..(480)

<400> SEQUENCE: 20 tgg atg gca tct act tcg tat gac tat tgc aga gtg ccc atg gaa gac        48
    Met Ala Ser Thr Ser Tyr Asp Tyr Cys Arg Val Pro Met Glu Asp
    1               5                   10                  15 ggg gat aag cgc tgt aag ctt ctg ctg ggg ata gga att ctg gtg ctc        96
Gly Asp Lys Arg Cys Lys Leu Leu Leu Gly Ile Gly Ile Leu Val Leu
                20                  25                  30 ctg atc atc gtg att ctg ggg gtg ccc ttg att atc ttc acc atc aag       144
Leu Ile Ile Val Ile Leu Gly Val Pro Leu Ile Ile Phe Thr Ile Lys
            35                  40                  45 gcc aac agc gag gcc tgc cgg gac ggc ctt cgg gca gtg atg gag tgt       192
Ala Asn Ser Glu Ala Cys Arg Asp Gly Leu Arg Ala Val Met Glu Cys
        50                  55                  60 cgc aat gtc acc cat ctc ctg caa caa gag ctg acc gag gcc cag aag       240
Arg Asn Val Thr His Leu Leu Gln Gln Glu Leu Thr Glu Ala Gln Lys
    65                  70                  75 ggc ttt cag gat gtg gag gcc cag gcc gcc acc tgc aac cac act gtg       288
Gly Phe Gln Asp Val Glu Ala Gln Ala Ala Thr Cys Asn His Thr Val
80                  85                  90                  95 atg gcc cta atg gct tcc ctg gat gca gag aag gcc caa gga caa aag       336
Met Ala Leu Met Ala Ser Leu Asp Ala Glu Lys Ala Gln Gly Gln Lys
                100                 105                 110 aaa gtg gag gag ctt gag gga gag atc act aca tta aac cat aag ctt       384
Lys Val Glu Glu Leu Glu Gly Glu Ile Thr Thr Leu Asn His Lys Leu
            115                 120                 125 cag gac gcg tct gca gag gtg gag cga ctg agg tca gag ata gcc ttc       432
Gln Asp Ala Ser Ala Glu Val Glu Arg Leu Arg Ser Glu Ile Ala Phe
        130                 135                 140 ccc cgc tac cct cca cct gcc aca ttc ctc tca ccc cca cat ccc tag       480
Pro Arg Tyr Pro Pro Pro Ala Thr Phe Leu Ser Pro Pro His Pro
    145                 150                 155

<210> SEQ ID NO 21
<211> LENGTH: 158
<212> TYPE: PRT
<213> ORGANISM: Homo sapiens

<400> SEQUENCE: 21

Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Leu Leu
                20                  25                  30
```

```
Ile Ile Val Ile Leu Gly Val Pro Leu Ile Ile Phe Thr Ile Lys Ala
        35                  40                  45

Asn Ser Glu Ala Cys Arg Asp Gly Leu Arg Ala Val Met Glu Cys Arg
    50                  55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Met
                85                  90                  95

Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Ser Glu Ile Ala Phe Pro
    130                 135                 140

Arg Tyr Pro Pro Pro Ala Thr Phe Leu Ser Pro Pro His Pro
145                 150                 155

<210> SEQ ID NO 22
<211> LENGTH: 314
<212> TYPE: DNA
<213> ORGANISM: Homo sapiens
<220> FEATURE:
<221> NAME/KEY: CDS
<222> LOCATION: (4)..(306)

<400> SEQUENCE: 22 tgg atg gca tct act tcg tat gac tat tgc aga gtg ccc atg gaa gac       48
    Met Ala Ser Thr Ser Tyr Asp Tyr Cys Arg Val Pro Met Glu Asp
    1               5                   10                  15 ggg gat aag cgc tgt aag ctt ctg ctg ggg ata gga att ctg gtg ctc       96
Gly Asp Lys Arg Cys Lys Leu Leu Leu Gly Ile Gly Ile Leu Val Leu
                20                  25                  30 ctg atc atc gtg att ctg ggg gtg ccc ttg att atc ttc acc atc aag      144
Leu Ile Ile Val Ile Leu Gly Val Pro Leu Ile Ile Phe Thr Ile Lys
            35                  40                  45 gcc aac agc gag gcc tgc cgg gac ggc ctt cgg gca gtg atg gag tgt      192
Ala Asn Ser Glu Ala Cys Arg Asp Gly Leu Arg Ala Val Met Glu Cys
        50                  55                  60 cgc aat gtc acc cat ctc ctg caa caa gag ctg acc gag gcc cag aag      240
Arg Asn Val Thr His Leu Leu Gln Gln Glu Leu Thr Glu Ala Gln Lys
65                  70                  75 ggc ttt cag gat gtg gag gcc cag gcc gcc acc tgc aac cac act gtg      288
Gly Phe Gln Asp Val Glu Ala Gln Ala Ala Thr Cys Asn His Thr Val
80                  85                  90                  95 gag aga tca cta cat taa accataag                                     314
Glu Arg Ser Leu His
            100

<210> SEQ ID NO 23
<211> LENGTH: 100
<212> TYPE: PRT
<213> ORGANISM: Homo sapiens

<400> SEQUENCE: 23

Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Leu Leu
                20                  25                  30

Ile Ile Val Ile Leu Gly Val Pro Leu Ile Ile Phe Thr Ile Lys Ala
            35                  40                  45
```

```
Asn Ser Glu Ala Cys Arg Asp Gly Leu Arg Ala Val Met Glu Cys Arg
    50                  55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Glu
                85                  90                  95

Arg Ser Leu His
            100

<210> SEQ ID NO 24
<211> LENGTH: 12
<212> TYPE: PRT
<213> ORGANISM: Homo sapiens

<400> SEQUENCE: 24

Leu Glu Gly Glu Ile Thr Thr Leu Asn His Lys Leu
1               5                   10

<210> SEQ ID NO 25
<211> LENGTH: 1389
<212> TYPE: DNA
<213> ORGANISM: Artificial
<220> FEATURE:
<223> OTHER INFORMATION: An artificially synthesized nucleotide sequence

<400> SEQUENCE: 25
atgaaagtgt tgagtctgtt gtacctgttg acagccattc ctggtatcct gtctgatgta      60
cagcttcagg agtcaggacc tggcctcgtg aaaccttctc agtctctgtc tctcacctgc     120
tctgtcactg gctactccat caccagtggt tattactgga actggatccg gcagtttcca     180
ggaaacaaac tggaatggat gggctacata agctacgacg gtagcaataa ctacaaccca     240
tctctcaaaa atcgaatctc catcactcgt gacacatcta agaaccagtt tttcctgaag     300
ttgaattctg tgactactga ggacacagct acatattact gtgcaattct gggacgcggc     360
tactggggcc aaggcaccac tctcacagtc tcctcagcct ccaccaaggg cccatcggtc     420
ttccccctgg cacctcctc caagagcacc tctggggca gcggccct gggctgcctg          480
gtcaaggact acttccccga accggtgacg gtgtcgtgga actcaggcgc cctgaccagc     540
ggcgtgcaca ccttcccggc tgtcctacag tcctcaggac tctactccct cagcagcgtg     600
gtgaccgtgc cctccagcag cttgggcacc cagacctaca tctgcaacgt gaatcacaag     660
cccagcaaca ccaaggtgga caagaaagtt gagcccaaat cttgtgacaa aactcacaca     720
tgcccaccgt gcccagcacc tgaactcctg ggggaccgt cagtcttcct cttcccccca     780
aaacccaagg acaccctcat gatctcccgg acccctgagg tcacatgcgt ggtggtggac     840
gtgagccacg aagaccctga ggtcaagttc aactggtacg tggacggcgt ggaggtgcat     900
aatgccaaga caaagccgcg ggaggagcag tacaacagca cgtaccgtgt ggtcagcgtc     960
ctcaccgtcc tgcaccagga ctggctgaat ggcaaggagt acaagtgcaa ggtctccaac    1020
aaagccctcc cagcccccat cgagaaaacc atctccaaag ccaaagggca gccccgagaa    1080
ccacaggtgt acaccctgcc cccatcccgg gatgagctga ccaagaacca ggtcagcctg    1140
acctgcctgg tcaaaggctt ctatcccagc gacatcgccg tggagtggga gagcaatggg    1200
cagccggaga acaactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga gagcctctc cctgtctccg    1380
ggtaaatga                                                            1389
```

<210> SEQ ID NO 26
<211> LENGTH: 462
<212> TYPE: PRT
<213> ORGANISM: Artificial
<220> FEATURE:
<223> OTHER INFORMATION: An artificially synthesized peptide sequence

<400> SEQUENCE: 26

Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Ser Val Thr Gly Tyr Ser Ile Thr
            35                  40                  45

Ser Gly Tyr Tyr Trp Asn Trp Ile Arg Gln Phe Pro Gly Asn Lys Leu
        50                  55                  60

Glu Trp Met Gly Tyr Ile Ser Tyr Asp Gly Ser Asn Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Ala Thr Tyr
                100                 105                 110

Tyr Cys Ala Ile Leu Gly Arg Gly Tyr Trp Gly Gln Gly Thr Thr Leu
            115                 120                 125

Thr Val Ser Ser Ala Ser Thr Lys Gly Pro Ser Val Phe Pro Leu Ala
        130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
        210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

```
Ser Arg Asp Glu Leu Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
        450                 455                 460

<210> SEQ ID NO 27
<211> LENGTH: 717
<212> TYPE: DNA
<213> ORGANISM: Artificial
<220> FEATURE:
<223> OTHER INFORMATION: An artificially synthesized nucleotide sequence

<400> SEQUENCE: 27
atggagacag acacactcct gctatgggtg ctgctgctct gggttccagg ttccactggt      60
gacattgtgc tgacacagtc tcctgcttcc ttagctgtat ctctggggca gagggccacc     120
atctcatgca gggccagcca aagtgtcagt acatctagct atagttatat gcactggtac     180
caacagaaac aggacagcc acccaaactc ctcatcaagt atgcatccaa cctagaatct     240
ggggtccctg ccaggttcag tggcagtggg tctgggacag acttcaccct caacatccat     300
cctgtggagg aggaggatac tgcaacatat tactgtcagc acagttggga gattccgtac     360
acgttcggag gggggaccaa gctggaaata aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc      660 acccatcagg gcctgagctc gcccgtcaca aagagcttca caggggaga gtgctag        717

<210> SEQ ID NO 28
<211> LENGTH: 238
<212> TYPE: PRT
<213> ORGANISM: Artificial
<220> FEATURE:
<223> OTHER INFORMATION: An artificially synthesized peptide sequence

<400> SEQUENCE: 28

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Gln Ser
        35                  40                  45

Val Ser Thr Ser Ser Tyr Ser Tyr Met His Trp Tyr Gln Gln Lys Pro
    50                  55                  60

Gly Gln Pro Pro Lys Leu Leu Ile Lys Tyr Ala Ser Asn Leu Glu Ser
65                  70                  75                  80

Gly Val Pro Ala Arg Phe Ser Gly Ser Gly Ser Gly Thr Asp Phe Thr
                85                  90                  95
```

```
Leu Asn Ile His Pro Val Glu Glu Asp Thr Ala Thr Tyr Tyr Cys
            100                 105                 110

Gln His Ser Trp Glu Ile Pro Tyr Thr Phe Gly Gly Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235
```

<210> SEQ ID NO 29
<211> LENGTH: 50
<212> TYPE: DNA
<213> ORGANISM: Artificial
<220> FEATURE:
<223> OTHER INFORMATION: An artificially synthesized primer sequence

<400> SEQUENCE: 29
aaagcggccg cgccgccacc atgaaagtgt tgagtctgtt gtacctgttg       50

<210> SEQ ID NO 30
<211> LENGTH: 39
<212> TYPE: DNA
<213> ORGANISM: Artificial
<220> FEATURE:
<223> OTHER INFORMATION: An artificially synthesized primer sequence

<400> SEQUENCE: 30
ctagtctaga tgaggagact gtgagagtgg tgccttggc                   39

<210> SEQ ID NO 31
<211> LENGTH: 33
<212> TYPE: DNA
<213> ORGANISM: Artificial
<220> FEATURE:
<223> OTHER INFORMATION: An artificially synthesized primer sequence

<400> SEQUENCE: 31
gtctcctcag cctccaccaa gggcccatcg gtc                         33

<210> SEQ ID NO 32
<211> LENGTH: 37
<212> TYPE: DNA
<213> ORGANISM: Artificial
<220> FEATURE:
<223> OTHER INFORMATION: An artificially synthesized primer sequence

<400> SEQUENCE: 32
tgatcatcat ttacccggag acagggagag gctcttc                     37

<210> SEQ ID NO 33
<211> LENGTH: 42
<212> TYPE: DNA
<213> ORGANISM: Artificial

```
<220> FEATURE:
<223> OTHER INFORMATION: An artificially synthesized primer sequence

<400> SEQUENCE: 33
aaagcggccg cgccgccacc atggagacag acacactcct gc          42

<210> SEQ ID NO 34
<211> LENGTH: 40
<212> TYPE: DNA
<213> ORGANISM: Artificial
<220> FEATURE:
<223> OTHER INFORMATION: An artificially synthesized primer sequence

<400> SEQUENCE: 34
ctagtctaga cgttttattt ccagcttggt cccccctccg             40

<210> SEQ ID NO 35
<211> LENGTH: 43
<212> TYPE: DNA
<213> ORGANISM: Artificial
<220> FEATURE:
<223> OTHER INFORMATION: An artificially synthesized primer sequence

<400> SEQUENCE: 35
aaataaaacg aactgtggct gcaccatctg tcttcatctt ccc         43

<210> SEQ ID NO 36
<211> LENGTH: 39
<212> TYPE: DNA
<213> ORGANISM: Artificial
<220> FEATURE:
<223> OTHER INFORMATION: An artificially synthesized primer sequence

<400> SEQUENCE: 36
tgatcactag cactctcccc tgttgaagct ctttgtgac              39

<210> SEQ ID NO 37
<211> LENGTH: 15
<212> TYPE: PRT
<213> ORGANISM: Homo sapiens

<400> SEQUENCE: 37

Glu Val Glu Arg Leu Arg Arg Glu Asn Gln Val Leu Ser Val Arg
1               5                   10                  15
```

ANTI-BST2 ANTIBODY

TECHNICAL FIELD

The present invention relates to antibodies that bind to human BST2 antigen, and uses thereof.

BACKGROUND ART

BST2 is known to be a transmembrane glycoprotein that is expressed at high levels in various cancer cells including myeloma (Non-patent Documents 1 to 4). To date, BST2 antigen has been reported to include several splicing variants (Patent Documents 1 and 5). It is also known that of these variants, BST2D is expressed at high levels in tumors (Non-patent Document 1). It is also known that anti-BST2 monoclonal antibody exhibits cytotoxicity against cells by binding to BST2 expressed on the cell surface (corresponding to the molecular species BST2D) (Non-patent Document 2). Furthermore, there have been attempts to develop antitumor agents that target tumor cells in vivo based on this principle. For example, the agents have been demonstrated to produce a superior antitumor effect which is expected to shrink or eradicate tumors in model mice grafted with human myeloma cells (Non-patent Documents 3 and 4).

Patent Document 1: WO 1999/043803
Patent Document 2: WO 1998/035698
Patent Document 3: WO 2002/064159
Patent Document 4: WO 2005/034994
Patent Document 5: WO 2006/008886
Patent Document 6: WO 2006/013923
Non-patent Document 1: Goto T. et al., Blood 84(6): 1922-30, 1994
Non-patent Document 2: Ohtomo T. et al., Biochem Biophys Res Commun. 258(3): 583-91, 1999
Non-patent Document 3: Ozaki S. et al., Blood 90(8): 3179-86, 1997
Non-patent Document 4: Koishihara Y. et al., Blood 92(s): 107, 1998

DISCLOSURE OF THE INVENTION

Problems to be Solved by the Invention

To date, several splicing variants have been reported for human BST2 antigen, which are listed below.

|  | Nucleotide sequence | Amino acid sequence | Length of amino acid sequence |
|---|---|---|---|
| Human BST2D | SEQ ID NO: 1 | SEQ ID NO: 2 | (180) |
| Human BST2H | SEQ ID NO: 20 | SEQ ID NO: 21 | (158) |
| Human BST2HS | SEQ ID NO: 22 | SEQ ID NO: 23 | (100) |

Attempts that use antibodies recognizing human BST2D, which is one of the splicing variants, to treat some types of tumors such as myeloma have been reported. For example, "anti-HM1.24 antibody" is a representative anti-BST2 monoclonal antibody that has been demonstrated to be therapeutically effective against myeloma. The "anti-HM1.24 antibody" was established as a monoclonal antibody using human myeloma cells as an immunogen. The subsequent epitope analysis revealed that the "anti-HM1.24 antibody" recognizes amino acids from positions 116 to 127 (SEQ ID NO: 24) of human BST2D shown in SEQ ID NO: 2. The amino acid sequence of this region is shared by human BST2H (FIG. 1).

An antibody having such antigen-recognition specificity is likely to bind to cells and tissues expressing BST2H as well. Specifically, for example, diagnostic tests may detect cells expressing BST2H in addition to tumors expressing human BST2D. Furthermore, because it also binds to BST2H-expressing cells, the blood concentration of the antibody may be decreased when applied therapeutically. An objective of the present invention is to solve this problem. Specifically, an objective of the present invention is to provide antibodies that specifically bind to human BST2D and uses thereof.

Means for Solving the Problems

The present inventors speculated that when administered to a human, non-specific adsorption of anti-HM1.24 antibody by tissues other than tumors in the human body may occur, and the blood concentration of the antibody may decrease. Thus, the present inventors aimed to find antibodies that recognize sequences other than the epitope recognized by anti-HM1.24 antibody. As a result of dedicated studies, the present inventors completed the present invention.

Specifically, the present inventors selected BST2 antibodies using as an indicator the binding between BST2 antibody and various splicing variants of human BST2 antigen, and successfully prepared specific anti-BST2 antibodies devoid of non-specific adsorption to tissues as a target of therapy or diagnosis. The use of the antibodies is expected to prevent decrease in the blood antibody level after administration. As a result, desired therapeutic effects can be produced even at an antibody dose lower than those of conventional antibodies. Alternatively, the antibody enables effective diagnosis for predicting the therapeutic effects.

Specifically, the present invention relates to anti-human BST2 antibodies, methods for producing them, and uses thereof as described below:

[1] an anti-human BST2 antibody that binds to human BST2D antigen but does not bind substantially to human BST2H antigen, or a fragment comprising the antigen-binding domain thereof;

[2] the antibody of [1] that recognizes a polypeptide comprising the amino acid sequence of SEQ ID NO: 3, or a fragment comprising the antigen-binding domain thereof;

[3] an antibody prepared using as an immunogen a peptide comprising the entire amino acid sequence of SEQ ID NO: 3 or at least five or more consecutive amino acids of SEQ ID NO: 3, or a fragment comprising the antigen-binding domain thereof;

[4] an antibody that binds to the same epitope in BST2D protein as the antibody of any of [1] to [3], or a fragment comprising the antigen-binding domain thereof;

[5] the antibody of any of [1] to [4] that is a monoclonal antibody, or a fragment comprising the antigen-binding domain thereof;

[6] a monoclonal antibody produced by hybridoma BST2#4LD deposited under the accession number FERM AP-21303, or a fragment comprising the antigen-binding domain thereof;

[7] the antibody of [1] whose heavy-chain and light-chain variable regions comprise as CDR1, CDR2, and CDR3 the following amino acid sequences:

```
heavy-chain variable region CDR1:
                                    (SEQ ID NO: 4)
SGYYWN;

heavy-chain variable region CDR2:
                                    (SEQ ID NO: 5)
YISYDGSNNYNPSLKNR;
and heavy-chain variable region CDR3:
                                    (SEQ ID NO: 6)
ILGRGY;

light-chain variable region CDR1:
                                    (SEQ ID NO: 7)
RASQSVSTSSYSYMH;

light-chain variable region CDR2:
                                    (SEQ ID NO: 8)
YASNLES;
and light-chain variable region CDR3:
                                    (SEQ ID NO: 9)
QHSWEIPYT;
``` or a fragment comprising the antigen-binding domain thereof;

[8] the antibody of [1] which comprises the heavy-chain variable region of SEQ ID NO: 11 and the light-chain variable region of SEQ ID NO: 13, or a fragment comprising the antigen-binding domain thereof;

[9] an antibody with a substitution, deletion, addition, and/or insertion of one or more amino acids in the antibody of (A) or (B) below, which has an activity equivalent to that of the antibody of (A) or (B):

(A) an antibody whose heavy-chain and light-chain variable regions comprise as CDR1, CDR2, and CDR3 the following amino acid sequences:

```
heavy-chain variable region CDR1:
                                    (SEQ ID NO: 4)
SGYYWN;

heavy-chain variable region CDR2:
                                    (SEQ ID NO: 5)
YISYDGSNNYNPSLKNR;
and heavy-chain variable region CDR3:
                                    (SEQ ID NO: 6)
ILGRGY;

light-chain variable region CDR1:
                                    (SEQ ID NO: 7)
RASQSVSTSSYSYMH;

light-chain variable region CDR2:
                                    (SEQ ID NO: 8)
YASNLES;
and light-chain variable region CDR3:
                                    (SEQ ID NO: 9)
QHSWEIPYT;
or
```

(B) an antibody which comprises the heavy-chain variable region of SEQ ID NO: 11 and the light-chain variable region of SEQ ID NO: 13, or a fragment comprising the antigen-binding domain thereof;

[10] an antibody that binds to the same epitope in BST2D protein as the antibody of any of [7] to [9], or a fragment comprising the antigen-binding domain thereof;

[11] the antibody of any of [7] to [10] which is a monoclonal antibody or a fragment comprising the antigen-binding domain thereof;

[12] the antibody of any of [1] to [11] having CDC against a cell expressing human BST2D antigen on the cell surface, or a fragment comprising the antigen-binding domain thereof;

[13] the antibody of any of [1] to [11] having ADCC against a cell expressing human BST2D antigen on the cell surface, or a fragment comprising the antigen-binding domain thereof;

[14] a polynucleotide encoding the antibody of any of [7] to [9] or a fragment comprising the antigen-binding domain thereof;

[15] a vector carrying a polynucleotide encoding the antibody of any of [7] to [9] or a fragment comprising the antigen-binding domain thereof;

[16] a transformed cell harboring in an expressible manner the vector of [15];

[17] a method for producing the antibody of any of [7] to [9] or a fragment comprising the antigen-binding domain thereof, which comprises the steps of culturing the transformed cell of [16] and collecting the antibody or fragment comprising the antigen-binding domain thereof from the culture;

[18] a hybridoma that produces the antibody of any of [1] to [5];

[19] the hybridoma BST2#4LD deposited under the accession number FERM AP-21303;

[20] a method of antibody production comprising the steps of culturing the hybridoma of [19] and collecting the antibody from the culture;

[21] a method for producing an anti-human BST2D specific antibody, which comprises the steps of:
(1) contacting an anti-human BST2D antibody with either or both of human BST2H and human BST2HS; and
(2) collecting, as an anti-human BST2D specific antibody, an anti-human BST2D antibody having either or both of the reaction specificities of:
  (i) not binding to human BST2H; and
  (ii) not binding to human BST2HS;

[22] a method for producing an anti-human BST2D specific antibody, which comprises the steps of:
(1) immunizing a nonhuman animal with a peptide comprising the amino acid sequence of SEQ ID NO: 3 or at least five or more consecutive amino acids selected from the amino acid sequence of SEQ ID NO: 3; and
(2) collecting the antibody from the nonhuman animal of (1), or harvesting cells producing the antibody and collecting the antibody from the antibody-producing cells;

[23] a therapeutic agent for a disease caused by growth of a tissue expressing human BST2D antigen, which comprises as an active ingredient the antibody of any of [1] to [13] or a fragment comprising the antigen-binding domain thereof;

[24] a therapeutic agent against a tumor expressing human BST2D antigen, which comprises as an active ingredient the antibody of any of [1] to [13] or a fragment comprising the antigen-binding domain thereof;

[25] the therapeutic agent of [24], wherein the tumor is derived from a cell of bone marrow;

[26] the therapeutic agent of [25], wherein the tumor derived from a cell of bone marrow is myeloma;

[27] the therapeutic agent of [26], wherein the myeloma is multiple myeloma;

[28] a diagnostic agent for detecting a tissue expressing human BST2D antigen, which comprises the antibody of any of [1] to [13] or a fragment comprising the antigen-binding domain thereof;
[29] a diagnostic agent for detecting a tumor expressing human BST2D antigen, which comprises the antibody of any of [1] to [13] or a fragment comprising the antigen-binding domain thereof;
[30] the diagnostic agent of [29], wherein the tumor is derived from a cell of bone marrow;
[31] the diagnostic agent of [30], wherein the tumor derived from a cell of bone marrow is myeloma;
[32] the diagnostic agent of [31], wherein the myeloma is multiple myeloma;
[33] a method for treating tumor expressing human BST2D antigen, which comprises the step of administering the antibody of any of [1] to [13] or a fragment comprising the antigen-binding domain thereof; and
[34] use of the antibody of any of [1] to [13] or a fragment comprising the antigen-binding domain thereof in producing a pharmaceutical composition for treating tumor expressing human BST2D antigen.

Alternatively, the present invention relates to the use of the antibody of any one of [1] to [13] or a fragment comprising the antigen-binding domain thereof in treating tumors expressing human BST2D antigen. The present invention also relates to the use of the antibody of any one of [1] to [13] or a fragment comprising the antigen-binding domain thereof in producing pharmaceutical compositions for treating tumors expressing human BST2D antigen. Furthermore, the present invention provides methods for treating tumors expressing human BST2D antigen, which comprise the step of administering to patients the antibody of any one of [1] to [13] or a fragment comprising the antigen-binding domain thereof.

Furthermore, the present invention relates to the use of the antibody of any one of [1] to [13] or a fragment comprising the antigen-binding domain thereof in diagnosing tumors expressing human BST2D antigen. Alternatively, the present invention relates to the use of the antibody of any one of [1] to [13] or a fragment comprising the antigen-binding domain thereof in producing diagnostic agents for tumors expressing human BST2D antigen. The present invention also provides methods for detecting tumors expressing human BST2D antigen in the body, which comprise the step of administering to patients the antibody of any one of [1] to [13] or a fragment comprising the antigen-binding domain thereof.

In addition, the present invention provides methods for producing pharmaceutical compositions for treating tumors expressing human BST2D antigen, which comprise the step of formulating the antibody of any one of [1] to [13] or a fragment comprising the antigen-binding domain thereof with pharmaceutically acceptable carriers. Alternatively, the present invention relates to methods for producing diagnostic agents for detecting tumors expressing human BST2D antigen in the body, which comprise the step of formulating the antibody of any one of [1] to [13] or a fragment comprising the antigen-binding domain thereof with pharmaceutically acceptable carriers.

Effect of the Invention

The present invention provides anti-human BST2D specific antibodies. The antibodies of the present invention specifically bind to cells expressing human BST2D among several variants of human BST2. Human BST2 is known to include splicing variants such as BST2H, but the antibodies of the present invention are substantially incapable of binding to cells expressing human BST2H. Accordingly, the therapeutic use of the antibodies of the present invention can achieve therapeutic effects even at lower doses. Alternatively, the diagnostic use of the antibodies of the present invention enables more specific detection of BST2D-expressing cells such as myeloma cells.

DETAILED DESCRIPTION OF THE INVENTION

Figure 1:
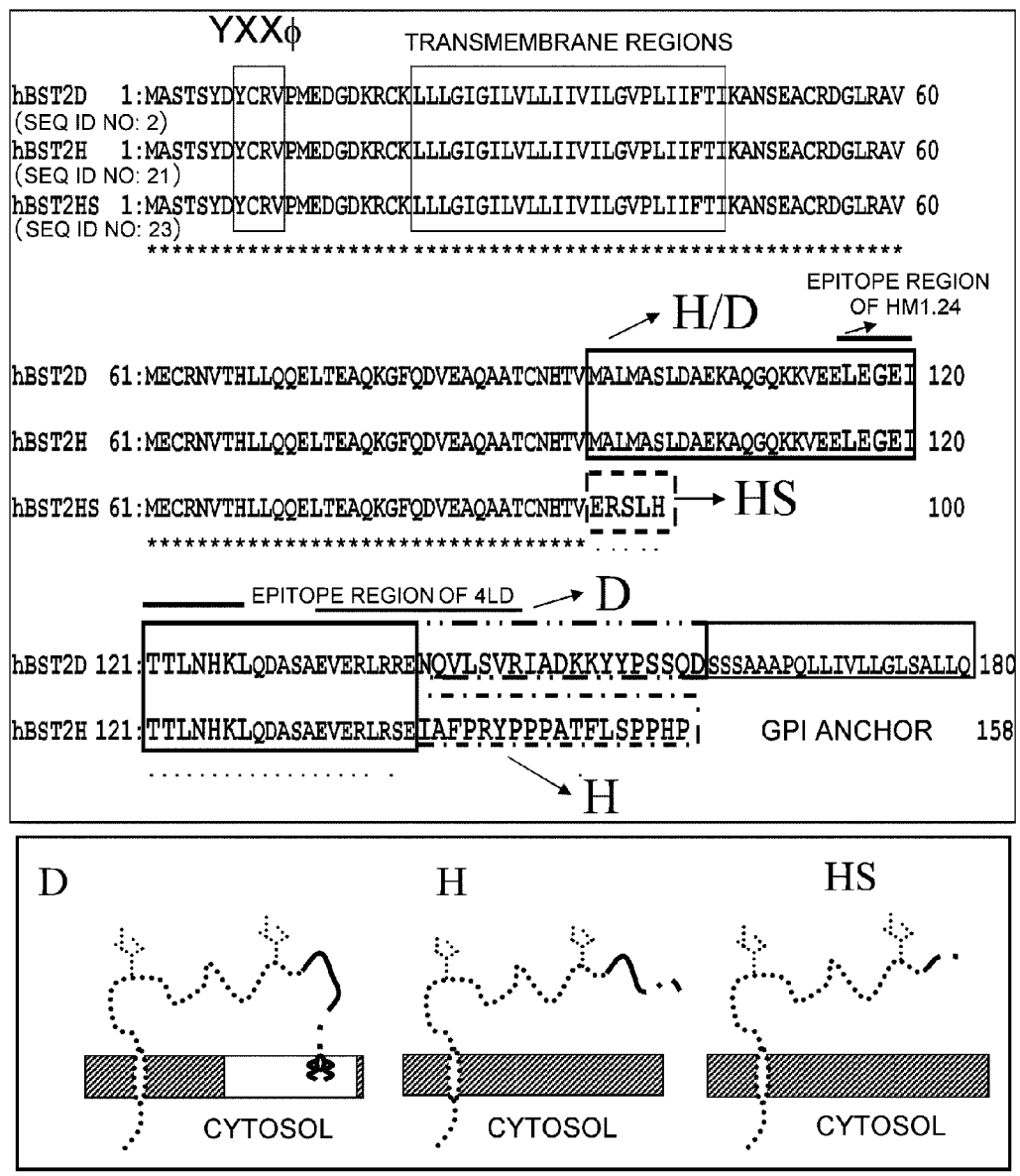
FIG. 1 presents diagrams showing the protein structures of BST2 splicing variants.

Examples of previously reported splicing variants of human BST2 antigen are shown in FIG. 1. The amino acid sequences of respective variants are shown in the following SEQ IDs:

|  | Nucleotide sequence | Amino acid sequence | Length of amino acid sequence |
|---|---|---|---|
| Human BST2D | SEQ ID NO: 1 | SEQ ID NO: 2 | (180) |
| Human BST2H | SEQ ID NO: 20 | SEQ ID NO: 21 | (158) |
| Human BST2HS | SEQ ID NO: 22 | SEQ ID NO: 23 | (100) |

When preparing monoclonal antibodies for use in the present invention, it is possible to use as an immunogen proteins comprising the amino acid sequence of SEQ ID NO: 2, or fragments thereof. The monoclonal antibodies of the present invention were revealed to recognize those proteins comprising the amino acid sequence of SEQ ID NO: 2 as an antigen. Thus, the monoclonal antibodies of the present invention can be prepared using these proteins as an immunogen.

Monoclonal antibodies of the present invention may be fragments of such monoclonal antibodies comprising their antigen-binding domains. A fragment comprising an antigen-binding domain refers to a fragment that comprises a portion responsible for the antigen binding of the antibody and retains antigen-binding activity. For example, antibody fragments comprising an antigen-binding domain produced by enzymatic digestion of an IgG can be used as the antibodies of the present invention. Specifically, antibody fragments such as Fab and F(ab')$_2$ can be prepared by papain or pepsin digestion. It is known that such antibody fragments can be applied as antibody molecules that have antigen-binding affinity.

Such fragments comprising an antigen-binding domain can be obtained not only by enzymatic cleavage but also by genetic engineering techniques. For example, antibody fragments comprising an antigen-binding domain can be prepared by isolating and expressing a gene encoding the antigen-binding domain. Specifically, antibodies constructed through genetic recombination can also be used in the present invention, as long as they retain necessary antigen-binding activities.

For example, such fragments are obtained through enzymatic digestion which cleaves at a specific amino acid sequence recognized by the enzyme. Alternatively, it is possible to prepare antibody fragments to comprise any desired region of an antibody by genetic engineering techniques. Thus, antibody fragments resulting from cleavage at a site different from those for antibody fragments such Fab and F(ab')$_2$ are also included in the fragments comprising the antigen-binding domain of an antibody of the present invention, as long as they retain the antigen-binding activity. Furthermore, reshaped antibody molecules prepared by re-linking a fragment comprising the antigen-binding domain to a constant region are also included in the antibodies of the present invention. Thus, antibodies generated by genetic recombination include, for example, chimeric antibodies, CDR-grafted antibodies, single-chain Fv, diabodies, linearized antibodies, and multi-specific antibodies produced from antibody fragments. Such antibodies can be generated from monoclonal antibodies or cells producing them by known methods.

Subclasses of antibodies with strong effector activity are known. Thus, the therapeutic effect of chimeric antibodies or CDR-grafted antibodies of the present invention can be further enhanced by selecting subclasses with superior effector activity.

Proteins comprising the amino acid sequence of SEQ ID NO: 2 can be prepared as a recombinant. For example, the nucleotide sequence of SEQ ID NO: 1 encodes the amino acid sequence of SEQ ID NO: 2. Accordingly, DNA comprising such a nucleotide sequence can be expressed using an appropriate vector and host to prepare the desired protein. Alternatively, it is possible to use as an immunogen an oligopeptide that comprises an amino acid sequence comprising consecutive amino acids selected from the amino acid sequence of SEQ ID NO: 2. The amino acid sequence to be selected as an immunogen comprises, for example, 7 to 50 amino acids, preferably about 5 to 20 amino acids.

As an immunogen in the present invention, the particularly preferred oligopeptide comprises an amino acid sequence selected from the human-BST2D-specific sequence (SEQ ID NO: 3). The human-BST2D-specific sequence refers to an amino acid sequence that is specific to the amino acid sequence of BST2D (SEQ ID NO: 2) and is not found in the amino acid sequences of other BST2 splicing variants, specifically, the amino acid sequences of BST2H (SEQ ID NO: 21) and BST2HS (SEQ ID NO: 23). More specifically, oligopeptides comprising an amino acid sequence of at least five or more consecutive amino acids selected from the amino acid sequence of SEQ ID NO: 3 (19 residues) serve as a preferred immunogen for preparing human-BST2D-specific antibodies of the present invention. The peptide to be used as an immunogen may comprise an extra amino acid sequence in addition to the amino acid sequence selected from BST2D, as long as it can induce BST2D-specific antibody. Specifically, the present invention relates to methods for producing anti-human BST2D specific antibodies, which comprise the steps of:

(1) immunizing a nonhuman animal with a peptide comprising the amino acid sequence of SEQ ID NO: 3 or an amino acid sequence comprising at least five or more consecutive amino acids selected from the amino acid sequence of SEQ ID NO: 3; and (2) collecting the antibody from the nonhuman animal of (1), or harvesting antibody-producing cells from the animal and collecting the antibody from the antibody-producing cells.

The human-BST2D-specific sequence (SEQ ID NO: 3) was identified based on multiple alignment of the amino acid sequences of BST2D, BST2H, and BST2HS proteins using ClustalW algorithm. The C terminus of mature BST2D protein was predicted using the GPI modification site prediction program ((1) GPI modification site prediction; (2) DGPI; and (3) GPI-SOM).

Methods for preparing oligopeptides comprising arbitrary amino acid sequences are known. Oligopeptides comprising a desired amino acid sequence can be prepared, for example, by chemically linking amino acids. Alternatively, fragments comprising a particular amino acid sequence can also be obtained by cleaving recombinant proteins comprising the full-length amino acid sequence, prepared as described above. The immunogenicity of the yielded oligopeptides can be increased by binding them with appropriate carrier proteins. Keyhole limpet hemocyanin, bovine serum albumin, and such can be used as carrier proteins.

As a next step, appropriate animals are immunized with an immunogen. The protein of SEQ ID NO: 2 or a peptide comprising a partial amino acid sequence thereof can be administered to animals to be immunized along with an adjuvant.

Furthermore, transformed cells that carry and are capable of expressing DNAs encoding the amino acid sequence of SEQ ID NO: 2 can also be used as an immunogen, and for example, DNAs comprising a nucleotide sequence constituting a coding region of the nucleotide sequence of SEQ ID NO: 1 are preferred. Transformed cells useful as an immunogen can be yielded by inserting the DNAs into an appropriate expression vector and transforming host cells with the construct.

Such host cells for use as an immunogen may be derived from the same animal species as the animal to be immunized. Immune responses specific to the foreign protein can be induced by using cells from the same species. For example, when rats are used as the animal to be immunized, rat-derived host cells can be used. Fractions of transformed cells comprising the above proteins can also be used as an immunogen. As shown in the Examples, a transmembrane domain is found in the amino acid sequence of SEQ ID NO: 2 (the transmembrane region shown in FIG. 1). Thus, proteins comprising the amino acid sequence may be expressed on cell membranes. Thus, membrane fractions of cells expressing the above proteins can be used as an immunogen.

As shown in FIG. 1, the extracellular domain of BST2D is presented on the surface of BST2D-expressing cells. This domain also contains a structure shared by other BST2 variants. Thus, antibodies that bind to variants other than BST2D may be generated when BST2D-expressing cells are used as an immunogen. However, a desired antibody can be obtained through antibody selection using the binding specificity to each variant as an indicator. Specifically, the present invention provides methods for producing anti-human BST2D specific antibodies, which comprise the steps of:

(1) contacting anti-human BST2D antibody with either or both of human BST2H and human BST2HS; and
(2) collecting as an anti-human BST2D specific antibody, an anti-human BST2D antibody having either or both of the reaction specificities of:
(i) incapable of binding to human BST2H; and
(ii) incapable of binding to human BST2HS.

The specificity of reaction between an antibody and each variant can be tested by the method described later.

Any nonhuman vertebrates can be used as the animal to be immunized according to the present invention. When preparing monoclonal antibodies, it is advantageous to use animals for which hybridoma-fusion partner can be easily obtained. For example, hybridomas have been established using cells derived from mice, rats, rabbits, bovines, goats, and such. Such animals can be used for immunization in the present invention. Adjuvants include, for example, Freund's complete and incomplete adjuvants.

Animals are immunized multiple times at three- to ten-day intervals. An arbitrary number of transformed cells may be used in each immunization. Typically, $10^3$ to $10^8$ transformed cells, for example, $10^6$ transformed cells are used in each immunization. Alternatively, 1 to 100 µg is generally used in immunization with a protein or peptide. Monoclonal antibodies of the present invention can be yielded by collecting immunocompetent cells from animals that have been immunized several times and then cloning cells that produce the desired antibodies. "Immunocompetent cells" refers to cells with the ability to produce antibodies in immune animals.

Such immunocompetent cells can be cloned, for example, by hybridoma methods. A single immunocompetent cell produces a single type of antibody. Therefore, monoclonal antibodies can be prepared when a cell population derived from a single cell can be established (cloned). Hybridoma methods refer to methods that comprise immortalization of immunocompetent cells by fusion with an appropriate cell line, followed by cloning. Many cell lines useful in the hybridoma method are known. Such cell lines have superior immortalization efficiency for lymphocytic cells, and comprise various genetic markers required for selection of cells that succeeded in cell fusion. Furthermore, when aiming to obtain antibody-producing cells, cell lines lacking antibody-producing ability can be used.

For example, mouse myeloma P3×63Ag8.653 (ATCC CRL-1580) is a commonly used cell line useful in cell fusion methods for mice and rat cells. Hybridomas are generally prepared by fusing cells from the same species; however, monoclonal antibodies can also be obtained from hetero-hybridomas between related but different species.

Specific protocols for cell fusion are known. Specifically, immunocompetent cells from immune animals are combined with appropriate fusion partners to achieve cell fusion. The immunocompetent cells include spleen cells and peripheral blood B cells. Various cell lines, described above, can be used as fusion partners. The polyethylene glycol method and the electrofusion method can be used to achieve cell fusion.

Next, cells that succeeded in cell fusion are selected using selection markers comprised by the fused cells. For example, when using HAT-sensitive cell lines for cell fusion, cells that succeeded in cell fusion are selected by selecting cells that can grow in HAT medium. The antibodies produced by selected cells are then confirmed to have the desired reactivity. Each hybridoma is screened based on antibody reactivity. Specifically, hybridomas are selected which produce an anti-human BST2D monoclonal antibody that does not recognize the epitope of amino acid positions 116 to 127 (SEQ ID NO: 24) in human BST2D of SEQ ID NO: 2. In hybridoma selection, antibodies produced by hybridomas are tested for their binding to human BST2D antigen, and then for their lack of ability to recognize the epitope of SEQ ID NO: 24 as binding site. In the present invention, the "lack of ability to recognize as epitope" or "lack of ability to recognize the epitope as binding site" can be tested by assessing the activity of binding to a polypeptide comprising the amino acid sequence of SEQ ID NO: 24 with the method described below.

Specifically, methods for assessing the activity of binding to a polypeptide comprising the amino acid sequence of SEQ ID NO: 24 include appropriate methods well known to those skilled in the art, such as enzyme-linked immunosorbent assay (ELISA), radioimmunoassay (RIA), enzyme immunoassay (EIA), and flow cytometry (FACS).

More specifically, such methods include, for example, methods for testing the lack of ability to bind BST2H or methods for testing the activity of binding to BST2HS. In methods that use ELISA with an enzyme-labeled antibody, BST2D or BST2H antigen is immobilized onto an appropriate solid phase; and then monoclonal antibody bound to the antigen is detected with the labeled antibody that recognizes immunoglobulin of the immunized animal. Hybridomas producing a monoclonal antibody can be screened rapidly by ELISA using microplates immobilized with BST2D or BST2H antigen on their inner walls. Then, hybridomas are assessed by the same procedure as ELISA assay for their activity to bind BST2H immobilized on an appropriate solid phase. Hybridomas producing a monoclonal antibody with desired binding activity can be selected from monoclonal antibodies that bind to BST2D antigen by this ELISA method.

Antibodies that bind to human BST2D but are substantially incapable of binding to human BST2H can be selected as described above. More specifically, as used herein, an antibody substantially incapable of binding to human BST2H refers to an antibody substantially incapable of binding to cells expressing human BST2H. Whether an antibody is substantially incapable of binding to cells expressing human BST2H can be tested by a method described later.

When the selected hybridoma is confirmed to produce a desired antibody by preferably subcloning, it can be selected as a hybridoma producing a monoclonal antibody of the present invention. Methods for measuring and assessing the antigen-binding activity of an antibody include the above-described ELISA and other appropriate methods such as FACS. Methods using FACS are particularly suitable for measuring and assessing antibody binding to an antigen expressed on the surface of cells suspended in buffer or the like. Flow cytometers used in the FACS methods include, for example, the following known devices:

FACSCanto™ II
FACSAria™
FACSArray™
FACSVantage™ SE
FACSCalibur™
(all are names of BD Biosciences products)
EPICS ALTRA HyPerSort
Cytomics FC 500
EPICS XL-MCL ADC, EPICS XL ADC
Cell Lab Quanta/Cell Lab Quanta SC
(all are names of Beckman Coulter products)

Preferred methods for measuring the antigen binding activity of anti-BST2 antibody include, for example, the method described below. First, a test antibody is reacted with cells expressing BST2D, BST2H, or BST2HS, and the test antibody is stained with an FITC-labeled secondary antibody that recognizes it. Then, the fluorescence intensity and cell count are determined using FACSCalibur (BD Biosciences). The amount of antibody bound to the cells is reflected in the fluorescence intensity (i.e., the value of geometric mean) obtained through analysis using CELL QUEST Software (BD Biosciences). Specifically, the binding activity of an antibody, which is represented by the amount of bound antibody, can be assessed by determining the value of the geometric mean.

In this method, whether an antibody is "substantially incapable of binding to BST2H-expressing cells" can be assessed, for example, by the method described below. First, a test antibody bound to cells expressing the BST2H molecule is stained with a secondary antibody. For example, when the test antibody is a mouse antibody, an FITC-labeled anti-mouse immunoglobulin antibody can be used as the secondary antibody. Then, the fluorescence intensity on the cells is determined. When FACSCalibur is used in flow cytometry for fluorescence detection, the resulting fluorescence intensity can be analyzed using CELL QUEST Software. From the values of geometric mean in the presence and absence of the test antibody, the ratio (ΔGeo-Mean) is calculated according to the formula shown below. The percent increase in the fluorescence intensity resulting from the binding of the test antibody can be determined from the ratio.

(ΔGeo-Mean)=[(Geo-Mean, in the presence of test antibody)]/[(Geo-Mean, in the absence of test antibody)]

The geometric mean (value of BST2HΔGeo-Mean) determined by the analysis, which reflects the amount of test antibody bound to BST2H-expressing cells, is compared to the value of ΔGeo-Mean ratio that reflects the amount of test antibody bound to cells expressing BST2D or BST2H. The anti-HM1.24 antibody may be used as a control antibody.

In the present invention, a test antibody is assumed to be "substantially incapable of binding to cells expressing BST2H", when the ΔGeo-Mean value of the test antibody in binding to cells expressing BSH2H is maximally 50%, preferably 30%, more preferably 20%, still more preferably less than 10% of the ΔGeo-Mean value of the test antibody in binding to cells expressing BST2D or BST2HS. The formula for determining the Geo-Mean value (geometric mean) is described in CELL QUEST Software User's Guide (BD biosciences). The activity of binding to cells expressing BST2H can be assessed by the same method. When cells expressing the BST2HS, BST2H, or BST2D molecule are used to assess known binding activity, it is preferred that each of them is prepared using the same expression vector and host cells, and that the expression levels in the respective cells are comparable to each other.

The monoclonal antibodies of the present invention include monoclonal antibodies that bind to cells expressing BST2D and whose activity of binding to cells expressing the BST2H molecule is lower than that of the activity of binding to BST2D-expressing cells. Alternatively, preferred monoclonal antibodies of the present invention include monoclonal antibodies that bind to cells expressing BST2D but are substantially incapable of binding to cells expressing the BST2H molecule.

Furthermore, the present invention provides antibodies that bind to the same epitopes as the monoclonal antibodies disclosed herein. Specifically, the present invention relates to antibodies that recognize the same epitopes as the monoclonal antibodies of the present invention, and uses thereof. For example, 4LD, which is a preferred monoclonal antibody of the present invention, recognizes as an epitope the amino acid sequence of EVERLRRENQVLSVR shown in SEQ ID NO: 37. More specifically, of the synthetic peptides constituted by a sequence of consecutive amino acids selected from the amino acid sequence (47-180) constituting the extracellular domain in the amino acid sequence of the whole human BST2D shown in SEQ ID NO: 2, K(47)---R(147) is recognized by the antibody of the present invention 4LD, while binding of the antibody 4LD to K(47)--V(146) is not detectable under the same conditions. Alternatively, E(133)---Q(180) is recognized by the antibody of the present invention 4LD, while binding of the antibody 4LD to V(134)----Q(180) is not detectable under the same conditions.

Thus, monoclonal antibodies that recognize the epitope constituted by EVERLRRENQVLSVR of SEQ ID NO: 37 are preferred monoclonal antibodies of the present invention. More specifically, of the synthetic peptides constituted by a sequence of consecutive amino acids selected from the amino acid sequence (47-180) constituting the extracellular domain in the amino acid sequence of whole human BST2D shown in SEQ ID NO: 2, antibodies that bind to a peptide consisting of K(47)---R(147) or E(133)---Q(180) and whose binding to K(47)--V(146) and V(134)---Q(180) is undetectable under the same conditions are preferred BST2D antibodies of the present invention. Such antibodies can be prepared, for example, by the methods described below.

Whether a test antibody binds to the same epitope as a different antibody, specifically, whether a test antibody shares the same epitope with a different antibody can be tested by assessing competition of the two in binding to the same epitope. In the present invention, the competition between antibodies can be detected by FACS, cross-blocking assay, or the like. In FACS, first, fluorescent signals are measured after binding of monoclonal antibodies of the present invention to cells expressing BST2D. Then, following reaction of a candidate antibody competitor, the same cells are reacted with monoclonal antibodies of the present invention, and analyzed by FACS using the same method. Alternatively, monoclonal antibodies of the present invention and a test competitor antibody may simultaneously react with the same cells. When the FACS analysis pattern of a monoclonal antibody of the present invention is changed upon addition of a competitor antibody, the competitor antibody and monoclonal antibody of the present invention are assessed to recognize the same epitope.

Furthermore, for example, competitive ELISA is a preferred cross-blocking assay. Specifically, in cross-blocking assay, cells expressing BST2D are immobilized onto wells of a microtiter plate. After preincubation in the presence or absence of a candidate competitor antibody, monoclonal antibodies of the present invention are added. The amount of a monoclonal antibody of the present invention bound to the cells expressing BST2D in a well is reverse-correlated with the binding activity of the candidate competitor antibody (test antibody) that competitively binds to the same epitope. Specifically, the greater the affinity a test antibody has for the same epitope, the smaller the amount of binding by the monoclonal antibody of the present invention to wells immobilized with cells expressing the BST2D protein. Conversely, the greater the affinity a test antibody has for the same epitope, the greater the amount of binding by the test antibody to wells immobilized with cells expressing the BST2D protein.

The amount of an antibody bound to a well can be readily determined by pre-labeling the antibody. For example, a biotin-labeled antibody can be measured using avidin-peroxidase conjugate and an appropriate substrate. In particular, a cross-blocking assay using enzyme labels such as peroxidase is called "competitive ELISA". Antibodies may be labeled with other labeling substances that enable detection or measurement. Specifically, radiolabels and fluorescent labels are known.

Alternatively, when the test antibody comprises a constant region derived from a species different from that of the monoclonal antibody of the present invention, either of the antibodies may be measured with a labeled antibody that specifically recognizes the constant region derived from either of the species. Alternatively, when the antibodies are derived from the same species but their antibody classes are different, the antibodies bound to a well may be measured by using antibodies that specifically recognize either of the classes.

When a candidate antibody blocks at least 20%, preferably at least 20 to 50%, and more preferably at least 50% of the binding of the monoclonal antibody of the present invention as compared to the binding activity determined in a control test conducted in the absence of the candidate competitor antibody, the candidate competitor antibody binds to substantially the same epitope as the monoclonal antibody of the present invention or competitively binds to the same epitope.

Antibodies that bind to the same epitope as the monoclonal antibody include, for example, the antibodies of [4] and [10] described above.

As described above, the antibodies of [4] and [10] include not only monovalent but also multivalent antibodies. The multivalent antibodies of the present invention include multivalent antibodies in which all of the antigen-binding domains are the same, and multivalent antibodies in which some or all of the antigen-binding domains are different from each other.

Any antibody that recognizes BST2D can be used as the antibody of the present invention. Preferred antibodies include, for example, the antibodies of (1) to (5) described below. These antibodies may be, for example, whole antibodies, minibodies, animal antibodies, chimeric antibodies, humanized antibodies, or human antibodies.

(1) An antibody whose heavy-chain and light-chain variable regions comprise as CDR1, CDR2, and CDR3 the following amino acid sequences, or a fragment comprising the antigen-binding domain thereof;

```
heavy-chain variable region CDR1:
                                    (SEQ ID NO: 4)
SGYYWN;

heavy-chain variable region CDR2:
                                    (SEQ ID NO: 5)
YISYDGSNNYNPSLKNR;
and heavy-chain variable region CDR3:
                                    (SEQ ID NO: 6)
ILGRGY;

light-chain variable region CDR1:
                                    (SEQ ID NO: 7)
RASQSVSTSSYSYMH;

light-chain variable region CDR2:
                                    (SEQ ID NO: 8)
YASNLES;
and light-chain variable region CDR3:
                                    (SEQ ID NO: 9)
QHSWEIPYT.
```

(2) The antibody of (1) which comprises the amino acid sequences described below as the heavy-chain and light-chain variable regions, or a fragment comprising the antigen-binding domain thereof:
the heavy-chain variable region of SEQ ID NO: 11 and the light-chain variable region of SEQ ID NO: 13.
(3) An antibody resulting from substitution, deletion, addition, and/or insertion of one or more amino acids in the antibody of (1) or (2), which has equivalent activity as the antibody of (1) or (2).
(4) An antibody that binds to the same epitope in BST2D protein as the antibody of any one of (1) to (3), or a fragment comprising the antigen-binding domain thereof.
(5) The antibody of any one of (1) to (5) which is a monoclonal antibody, or a fragment comprising the antigen-binding domain thereof.

A preferred embodiment of the antibody of (3) described above is antibodies without alteration in their CDRs. Of the antibodies of (3) described above, a preferred embodiment of "antibody resulting from substitution, deletion, addition, and/or insertion of one or more amino acids in the antibody of (1), which has equivalent activity as the antibody of (1)" is, for example, "antibodies resulting from substitution, deletion, addition, and/or insertion of one or more amino acids in the antibody of (1), which have equivalent activity as the antibody of (1), and whose heavy chain comprises the amino acid sequence of SEQ ID NO: 4 as CDR1, the amino acid sequence of SEQ ID NO: 5 as CDR2, and the amino acid sequence of SEQ ID NO: 6 as CDR3, and whose light chain comprises the amino acid sequence of SEQ ID NO: 7 as CDR1, the amino acid sequence of SEQ ID NO: 8 as CDR2, and the amino acid sequence of SEQ ID NO: 9 as CDR3". Of the antibodies of (3) described above, preferred embodiments of other antibodies can be presented in the same way.

Herein, the "antibody having an equivalent activity" refers to a "functionally equivalent antibody". The "equivalent activity" or "equivalent function" means, for example, that the BST2D- or BST2H-binding activity, affinity for BST2D or BST2H, or complement-dependent cytotoxicity (CDC) or antibody-dependent cell-mediated cytotoxicity (ADCC) against cells expressing the BST2D protein is the same between antibodies.

Methods for introducing mutations into polypeptides are known to those skilled in the art and included in the methods for preparing polypeptides functionally equivalent to a polypeptide. For example, those skilled in the art can prepare an antibody functionally equivalent to the antibody of the present invention by introducing appropriate mutations into the antibody using site-directed mutagenesis (Hashimoto-Gotoh, T. et al. (1995) Gene 152, 271-275; Zoller, M J. and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc Natl Acad Sci USA. 82, 488-492; and Kunkel (1988) Methods Enzymol. 85, 2763-2766). Alternatively, amino acid mutations may occur naturally. Antibodies that are functionally equivalent to the antibodies of the present invention and comprise an amino acid sequence comprising mutation of one or more amino acids in the amino acid sequence of an antibody of the present invention are also included in the antibodies of the present invention.

In such mutants, the number of amino acids that are mutated is generally 50 amino acids or less, preferably 30 or less, and more preferably 10 or less (for example, 5 amino acids or less).

An amino acid residue is preferably mutated into one that conserves the properties of the amino acid side chain. For example, based on their side chain properties, amino acids are classified into:

hydrophobic amino acids (A, I, L, M, F, P, W, Y, and V);

hydrophilic amino acids (R, D, N, C, E, Q, G, H, K, S, and T);

amino acids having aliphatic side-chains (G, A, V, L, I, and P);

amino acids having hydroxyl group-containing side-chains (S, T, and Y);

amino acids having sulfur atom-containing side-chains (C and M);

amino acids having carboxylic acid- and amide-containing side-chains (D, N, E, and Q);

base-containing side-chains (R, K, and H); and amino acids having aromatic-containing side-chains (H, F, Y, and W).

(The letters within parentheses indicate one-letter amino acid codes.)

Polypeptides comprising a modified amino acid sequence resulting from deletion, addition, and/or substitution of one or more amino acid residues in an amino acid sequence are known to retain original biological activity (Mark, D. F. et al., Proc. Natl. Acad. Sci. USA (1984) 81, 5662-5666; Zoller, M. J. and Smith, M., Nucleic Acids Research (1982) 10, 6487-6500; Wang, A. et al., Science 224, 1431-1433; and Dalbadie-McFarland, G. et al., Proc. Natl. Acad. Sci. USA (1982) 79, 6409-6413). Specifically, the activity of a polypeptide is in general likely to be retained in the amino acid sequence constituting the polypeptide when the amino acid substitution is between amino acids categorized in the same group. Herein, such a substitution between amino acids within an amino acid group is referred to as conservative substitution.

In the present invention, recombinant antibodies produced by genetic engineering techniques may be used as the antibody of the present invention. To produce the recombinant antibodies, the antibody genes are inserted into appropriate vectors, and then introduced into hosts (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, such an antibody can be expressed by isolating cDNA encoding the antigen-binding domain of an antibody from a hybridoma and inserting the cDNA into an appropriate expression vector. There are known techniques for obtaining cDNAs encoding antibody variable regions and inserting them into expression vectors, and then transforming appropriate host cells with the vectors and expressing the antibody. There are also known techniques for preparing chimeric antibodies by linking variable regions containing the antigen-binding domains to the constant regions.

The present invention also provides host cells introduced with vectors of the present invention. The host cells to which the vectors of the present invention are introduced are not particularly limited, and for example, *Escherichia coli* and various types of animal cells can be used. The host cells of the present invention can be used, for example, as a production system for expressing and producing the antibodies of the present invention. The systems for producing the polypeptides include in vitro and in vivo production systems. The in vitro production systems include production systems using eucaryotic or procaryotic cells.

When eucaryotic cells are used, for example, animal cells, plant cells, and fungal cells can be used as hosts. Such animal cells include mammalian cells (for example, CHO (J. Exp. Med. (1995) 108, 945), COS, NIH3T3, myeloma, baby hamster kidney (BHK), HeLa, and Vero), amphibian cells (for example, *Xenopus* oocyte (Valle, et al., Nature (1981) 291, 358-340)), and insect cells (for example, Sf9, Sf21, and Tn5). Among CHO cells, those particularly preferred are CHO cells deficient in the DHFR gene, dhfr-CHO (Proc. Natl. Acad. Sci. USA (1980) 77: 4216-4220) and CHO K-1 (Proc. Natl. Acad. Sci. USA (1968) 60: 1275). CHO cells are used particularly preferably for large-scale expression in animal cells. The vectors can be introduced into host cells, for example, using calcium phosphate methods, DEAE-dextran methods, methods using cationic liposome DOTAP (Boehringer-Mannheim), electroporation, and lipofection.

Known fungal cells include yeasts such as genus *Saccharomyces*, for example, *Saccharomyces cerevisiae*, and filamentous fungi such as genus *Aspergillus*, for example *Aspergillus niger*.

When using procaryotic cells, production systems using bacterial cells are available. Such bacterial cells include *E. coli*, for example, JM109, DH5α, and HB101. It is also possible to use *Bacillus subtilis*.

These cells are transformed with a polynucleotide of interest, and the resulting transformants are cultured in vitro to obtain the antibodies. The transformants can be cultured using known methods. Culture media for animal cells include, for example, DMEM, MEM, RPMI 1640, and IMDM. They may be used with or without a serum supplement such as fetal calf serum (FCS). Preferred pH of such a culture medium is about 6 and 8. In general, such cells are cultured at about 30 to 40° C. for about 15 to 200 hours, and the culture medium is changed, aerated, or stirred if necessary.

The antibodies of the present invention obtained as described above can be isolated from host cells or outside the cells (medium, etc.), and purified as a substantially pure homogeneous antibody. The antibodies can be separated and purified using conventional separation and purification methods for antibody purification, without limitation. For example, the antibodies can be separated and purified by appropriately selecting and combining column chromatography, filtration, ultrafiltration, salting out, solvent precipitation, solvent extraction, distillation, immunoprecipitation, SDS-polyacrylamide gel electrophoresis, isoelectrofocusing, dialysis, recrystallization, and such.

Chromatography includes, for example, affinity chromatography, ion exchange chromatography, hydrophobic chromatography, gel filtration, reverse phase chromatography, and adsorption chromatography (Strategies for Protein Purification and Characterization: A Laboratory Course Manual.

Ed Daniel R. Marshak et al., Cold Spring Harbor Laboratory Press, 1996). These chromatographic methods can be performed using liquid chromatography, for example, HPLC and FPLC. Columns used for affinity chromatography include protein A columns and protein G columns. Such Protein A columns include, for example, Hyper D, POROS, and Sepharose FF (Pharmacia). The present invention also includes antibodies highly purified using such purification methods.

Furthermore, the antigen-binding region of a monoclonal antibody can be transferred to other immunoglobulins. Antigen-binding regions in immunoglobulins are constituted by complementarity determining regions (CDRs) and frame regions. The antigen-binding specificity of each immunoglobulin is determined by its CDR, and the frame maintains the structure of the antigen-binding region. CDR amino acid sequences are extremely diverse, while frame region amino acid sequences are highly conserved. Antigen-binding specificity can also be transferred by inserting the CDR amino acid sequence into the frame region of another immunoglobulin molecule. Methods for transferring the antigen-binding specificity of nonhuman immunoglobulins into human immunoglobulins using the above methods have been established.

Any monoclonal antibody prepared as described above can be used in the present invention. Specifically, in the present invention, it is possible to use monoclonal antibodies which comprise immunoglobulins comprising antigen-binding regions encoded by polynucleotides derived from cDNAs that encode the antigen-binding regions of such monoclonal antibodies.

Hybridomas producing monoclonal antibodies that can be used in the present invention include, for example, hybridomas #4LD, #3LD, and #9LD. Hybridoma #4LD was deposited under depositary number FERM AP-21303 on Jun. 6, 2007 in the International Patent Organism Depositary, National Institute of Advanced Industrial Science and Technology, and further depository number FERM BP-10964 was assigned as an international deposit under Budapest Treaty. The deposition is specified by the following description:
(a) Name and Address of Depositary Institution
Name: International Patent Organism Depositary, National Institute of Advanced Industrial Science and Technology
Address: Tsukuba Central 6, 1-1-1 Higashi, Tsukuba, Ibaraki, Japan (Zip code: 305-8566)
(b) Date of Deposition: Jun. 6, 2007
(c) Depository Number: FERM BP-10964 (hybridoma #4LD)

Monoclonal antibodies for use in the present invention can be collected from cultures of hybridomas producing these monoclonal antibodies. Hybridomas may be cultured in vitro or in vivo. Hybridomas can be cultured in vitro using known culture medium such as RPMI1640. Immunoglobulins secreted from such hybridomas are accumulated in culture supernatants. Thus, monoclonal antibodies of the present invention can be prepared by collecting such culture supernatants, then purifying as required. Immunoglobulins can be purified more simply when serum-free media are used. However, media can be supplemented with about 10% fetal calf serum for rapid growth of hybridomas and enhanced antibody production.

Hybridomas can also be cultured in vivo. Specifically, by inoculating hybridomas into the peritoneal cavity of nude mice, hybridomas can be cultured in the peritoneal cavities. Monoclonal antibodies are accumulated in ascites. Thus, desired monoclonal antibodies can be obtained by collecting ascites, then purifying as required. The yielded monoclonal antibodies may be modified or processed appropriately for each purpose.

Antibodies may be chimeric or monoclonal.

The monoclonal antibodies of the present invention that specifically recognize BST2D include monoclonal antibodies that recognize proteins comprising the amino acid sequence of SEQ ID NO: 2 but not proteins comprising the amino acid sequence of SEQ ID NO: 21. Such antibodies can be obtained, for example, by selecting antibodies that bind under certain conditions to a polypeptide comprising the amino acid sequence of SEQ ID NO: 2 but whose binding to a polypeptide comprising the amino acid sequence of SEQ ID NO: 21 is undetectable under the same conditions. More specifically, desired antibodies can be selected, for example, by transforming cells with an expression vector that carries DNA encoding the amino acid sequence of SEQ ID NO: 2 or SEQ ID NO: 21, and comparing the cells in terms of antibody binding properties. Known methods such as FACS can be used to compare the properties of antibody binding to the transformed cells.

When an antibody that specifically recognizes BST2D is administered to a host heterologous to the species from which the antibody was derived, the antibody is preferably processed into a form hardly recognized as a foreign material by the host. For example, artificially modified recombinant antibodies such as chimeric and humanized antibodies can be used to reduce heterologous antigenicity against humans. These modified antibodies can be produced using known methods. The chimeric antibody is an antibody comprising the variable regions of the heavy and light chains of an antibody from a nonhuman mammal such as a mouse, and the constant regions of the heavy and light chains of a human antibody. The chimeric antibody can be produced by linking a DNA encoding the variable regions of the mouse antibody to a DNA encoding the constant regions of the human antibody, inserting this into an expression vector, and then introducing the vector into a host for expression.

Humanized antibodies are also referred to as "reshaped human antibodies". They are antibodies in which the complementarity determining region (CDR) of an antibody derived from a nonhuman mammal, for example a mouse, is grafted to the CDR of a human antibody, and general gene recombination procedures are known. When processed into the molecules described below, it becomes harder for an immunoglobulin to be recognized as a foreign material. Techniques for processing immunoglobulin molecules as described below are known.

fragments comprising an antigen-binding region that lacks a constant region (Monoclonal Antibodies: Principles and Practice, third edition, Academic Press Limited. 1995; Antibody Engineering, A Practical Approach, IRL PRESS, 1996)

chimeric antibodies composed of an antigen-binding region of a monoclonal antibody and a constant region of a host immunoglobulin (Experimental Manual for Gene Expression, Kodansha 1994 (eds., I. Ishida and T. Ando))

CDR-substituted antibodies in which a complementarity determining region (CDR) of a host immunoglobulin has been replaced with a CDR of a monoclonal antibody (Experimental Manual for Gene Expression, Kodansha 1994 (eds., I. Ishida and T. Ando))

Alternatively, a method to obtain human antibodies that do not have heterogeneticity against humans is also known. For example, human antibodies can be obtained from nonhuman immune animals introduced with human antibody genes. More specifically, transgenic mice introduced with human antibody genes are in practical use as immune animals for producing human antibodies (Ishida et al., Cloning and Stem Cells, 4: 85-95, 2002). Human antibodies recognizing BST2 can be prepared by using such animals with human BST2 as an antigen. Human antibodies are preferably administered to humans.

In addition, there is a known technique to obtain human antibodies by panning using human antibody libraries. Specifically, genes for the variable regions of human immunoglobulins can be obtained by the phage display method (McCafferty J. et al., Nature 348: 552-554, 1990; Kretzschmar T. et al., Curr Opin Biotechnol. 2002 December; 13(6): 598-602). The phage display method comprises integrating genes encoding the variable regions of human immunoglobulins into phage genes. Phage libraries can be prepared using various immunoglobulin genes as a source. Such variable regions are expressed as fusion proteins with proteins constituting phages. The variable regions expressed on phage surfaces by phages retain antigen-binding activity. Thus, phages expressing variable regions with desired binding activity can be screened from phage libraries by selecting phages that bind to antigens, cells expressing antigens, or the like. Furthermore, phage particles selected in this way carry genes that encode variable regions with desired binding activity. Specifically, genes encoding variable regions with desired binding activity can be obtained by the phage display method, using the variable region binding activity as an indicator.

Antibodies used in the present invention preferably include antibodies having cytotoxic activity.

In the present invention, the cytotoxic activity includes, for example, antibody-dependent cell-mediated cytotoxicity (ADCC) and complement-dependent cytotoxicity (CDC). Herein, CDC refers to cytotoxic activity of the complement system. ADCC refers to the activity of conferring damage to target cells when a specific antibody binds to an antigen on the target cell surface, and cells carrying Fcγ receptor (immune cells and others) bind to the Fc via Fcγ receptor.

Whether an anti-BST2D antibody has ADCC or CDC can be assessed by known methods (see, for example, Current protocols in Immunology, Chapter 7. Immunologic studies in humans, Editor, John E, Coligan et al., John Wiley & Sons, Inc. (1993)).

Specifically, first, effector cells, complement solutions, and target cells are prepared.
(1) Preparation of Effector Cells (Human Peripheral Mononuclear Cells)

Peripheral blood is obtained from healthy human donors. Peripheral mononuclear cells are isolated from the blood by the Ficoll method and used as effector cells.
(2) Preparation of Complement Solution Complement solutions can be prepared at a final complement concentration of 6% by diluting Baby Rabbit Complement (CEDARLANE) with CDC medium.
(3) Preparation of Target Cells BST2 protein-expressing cells such as CHO cells or human myeloma-derived RPMI8226 cells expressing the BST2D or BST2H protein may be used as target cells.

BST2 protein-expressing cells include cells transformed with a gene encoding the BST2 protein and various tumor cells.

ADCC and CDC can be determined by the methods described below.

CDC assay is carried out by adding the target cells and anti-BST2 antibody each at 50 µl/well into a 96-well round-bottomed plate. Then, 50 µl of a complement solution is added, and the plate is incubated in a carbon dioxide gas incubator at 37° C. for two hours. The final antibody concentration is adjusted to 0.01 µg/ml, 0.1 µg/ml, 1 µg/ml, or 10 µg/ml. The culture supernatants are collected after culture. The "amount (experimental sample) of LDH leakage from target cells due to the complement activity" is determined by measuring the level of LDH in each culture supernatant using CytoTox96™ Assay (PROMEGA).

CDC assay is carried out using the following controls:
(1) experimental LDH release (cytotoxicity of complement against target cells);
(2) spontaneous LDH release from target cells;
(3) maximum LDH release from target cells;
(4) normalization control for the liquid volume after addition of lysis solution; and
(5) background level in culture medium alone (blank).

Mean absorbance for the blank of (5) is subtracted from each mean value for absorbance determined for (1), (2), and (3). Then, CDC is calculated according to the following formula:

CDC(%)=[(experimental release)−(spontaneous release from target)]/[(maximum release from target)−(normalization control for target liquid volume)−(spontaneous release from target)]×100

ADCC assay is carried out by adding 50 ml/well of target cells (BST2(D)-CHO cells, human myeloma-derived cell line RPMI8226) (4×10$^5$/ml) into a 96-well round-bottomed plate. An anti-BST2 antibody solution is added at a final antibody concentration of 10 µg/ml. The cells are incubated at 4° C. for 30 minutes. The effector cells (PBMC) are added in an amount 12.5, 25, 50, or 100 times of that of target cells. The mixed cells are incubated at 37° C. for four hours. The LDH level in a cell supernatant is measured to determine the amount (experimental sample) of LDH leakage from target cells as a result of cytotoxicity. ADCC assay is carried out using controls similar to those for the CDC assay.

Various tumors expressing BST2D can be treated or prevented by administering BST2D-specific antibodies of the present invention. Specifically, the present invention provides methods for treating tumors expressing human BST2D, which comprise the step of administering to patients, antibodies or fragments comprising the antigen-binding domain thereof that bind to BST2D but are substantially incapable of binding to BST2H. Blood tumors that can be treated according to the present invention include those listed below. The blood tumors include hematopoietic tumors.

Leukemia
Myelodysplastic syndrome (MDS)
Malignant lymphoma
Chronic myeloid leukemia
Plasma cell dyscrasia
Myeloproliferative disorder Of the above blood tumors, plasma cell dyscrasia includes myeloma, multiple myeloma, and macroglobulinemia. The myeloproliferative disorder includes primary polycythemia, essential thrombocythemia, and agnogenic myeloid metaplasia. Among these blood tumors, myeloma, more specifically, multiple myeloma is a preferred therapeutic target. The antibodies of the present invention are expected to be particularly beneficial when administered to a living body, because they can specifically bind to cells that serve as the therapeutic or diagnostic target in the body without non-specific binding to tissues that are not targets of the therapy or diagnosis.

The present inventors revealed that the antibodies of the present invention have CDC and ADCC. Based on this finding, the present invention provides tumor therapeutic agents which comprise the antibodies of the present invention as an active ingredient. Furthermore, when used for therapeutic or preventive purposes, the antibodies of the present invention may be used after modification if needed. The antibodies of the present invention that specifically recognize the extracellular domain of human BST2D exhibit cytotoxicity against cells expressing BST2D. The cytotoxic effect on BST2D-expressing cells can be further potentiated by modifying the antibodies with cytotoxic agents. Such cytotoxic agents include the following substances:

Toxins: pseudomonas endotoxin (PE), diphtheria toxin, ricin

Radioisotopes: $Tc^{99m}$, $Sr^{89}$, $I^{131}$, $Y^{90}$

Anticancer agents: calicheamicin, mitomycin, paclitaxel

Toxins comprising proteins can be bound to antibodies, fragments thereof, or such using difunctional reagents. Alternatively, fusion proteins may be prepared by linking antibody-encoding genes with toxin-encoding genes. Methods for binding antibodies with radioisotopes are also known. For example, methods for labeling antibodies with radioisotopes using chelating agents are known. Furthermore, anticancer agents can be bound to antibodies using sugar chains or difunctional reagents.

The present invention provides therapeutic agents against tumors, which comprise an antibody of the present invention as an active ingredient. The antibodies of the present invention have CDC and ADCC, and are thus expected to be effective, in particular, for treating and preventing tumors such as cancers (blood tumors in particular).

When an antibody of the present invention is used as a therapeutic agent, liquid preparations comprising the antibody of the present invention can be administered, for example, intravenously or subcutaneously alone or in combination with other therapeutic agents. Such therapeutic agents used in combination include, for example, known therapeutic agents for multiple myeloma. Therapeutic agents that have been used to treat myeloma include those listed below.

| | | |
|---|---|---|
| Bortezomib | Thalidomide | Lenalidomide |
| Melphalan | Dexamethasone | Vincristine |
| Doxorubicin | Interferon-α | Rituximab |

Furthermore, therapeutic agents for enhancing the effect of antibodies can also used in addition to therapeutic agents for myeloma. For example, an immunopotentiating agent can be administered as an agent for enhancing the effector activity, together with the antibodies of the present invention. Specifically, the antibody's effector activity can be expected to be enhanced by administering an antibody of the present invention in combination with interferon-γ, interleukin-2, interleukin-12, or such. Alternatively, such an immunopotentiation effect can also be expected with Toll-like receptor agonist including CpG oligonucleotides.

An antibody or fragment thereof that specifically recognizes BST2D, or an antibody comprising at least the antigen-binding domain thereof can be administered in a form of a protein or a polynucleotide encoding it as a therapeutic agent of the present invention against tumors. When such a polynucleotide is administered, it is preferable to use a vector in which a polynucleotide encoding a protein of interest is arranged under the control of an appropriate promoter so as to express the protein of interest. Enhancers and terminators may also be arranged in the vector. There are known vectors carrying genes for the heavy and light chains constituting an immunoglobulin and capable of expressing an immunoglobulin molecule.

Vectors that can express immunoglobulins can be administered by introducing to cells. When administered to living bodies, vectors that can infect cells when administered to living bodies may be administered as they are. Alternatively, lymphocytes isolated from living bodies may be introduced with such vectors and then returned to the body (ex vivo).

Furthermore, when administering an immunoglobulin expression vector to a living body, plasmids separately carrying the heavy chain and light chain can be administered at a dose of 0.1 to 10 mg/kg weight for each plasmid, for example, 1 to 5 mg/kg weight for co-transfection. Such vectors can also be introduced into cells in vitro at a dose of 1 to 5 µg/$10^6$ cells.

The therapeutic agents of the present invention can be administered as pharmaceuticals, and may be administered systemically or locally via oral or parenteral administration. It is possible to select, for example, intravenous injections such as drip infusions, intramuscular injections, intraperitoneal injections, subcutaneous injections, suppositories, enemas, oral enteric tablets, or the like. Appropriate administration methods can be selected depending on a patient's age and symptoms. The dose of therapeutic agent to be administered to a living body in terms of monoclonal antibody is typically 0.5 mg to 100 mg immunoglobulin/kg weight, for example, 1 mg to 50 mg immunoglobulin/kg weight, and preferably 2 mg to 10 mg immunoglobulin/kg weight. The intervals between administrations of antibody to a living body can be appropriately regulated so that an effective in vivo concentration of immunoglobulin is maintained during the treatment. Specifically, administration can be at one to two week intervals, for example.

The administration route is arbitrary. Those skilled in the art can appropriately select effective administration routes for treatment. Specifically, administration can be oral or parenteral. For example, antibodies may be administered systemically or locally by intravenous, intramuscular, intraperitoneal, or subcutaneous injections, or such. In the present invention, preparations suitable for parenteral administration include injections, suppositories, and sprays. Alternatively, when added to cells, the immunoglobulins are typically added to culture media at a concentration of 1 µg/ml, preferably at 10 µg/ml or higher, more preferably at 50 µg/ml or higher, and still more preferably at 0.5 mg/ml or higher.

The agents for treating tumors of the present invention can be administered to a living body by any method. The monoclonal antibodies are generally formulated in combination with a pharmaceutically acceptable carrier and used as therapeutic agents. The therapeutic agents of the present invention may be combined with additives such as thickeners, stabilizers, preservatives, and solubilizing agents, if required. Such carriers or additives include lactose, citric acid, stearic acid, magnesium stearate, sucrose, starch, talc, gelatin, agar, vegetable oils, and ethylene glycol.

The phrase "pharmaceutically acceptable" means being approved by supervisory authorities of the government in each country, or described in terms of its use for animals, mammals, and in particular humans, in Pharmacopoeia in each country or generally known Pharmacopoeia. Such therapeutic agents of the present invention may also be provided in the form of single- or multiple-dose freeze-dried powders or tablets. Such freeze-dried powders or tablets may be combined with sterile water, physiological saline, or buffers for injection that are used to dissolve the composition to a desired concentration before administration.

Antibodies that specifically recognize human BST2D, which are provided by the present invention, can be used to detect cells expressing human BST2D. Diseases caused by cells expressing BST2D can be diagnosed, for example, by detecting cells expressing human BST2D in a body or in tissues collected from a human body. Specifically, the present invention relates to diagnostic agents for detecting tissues expressing a human BST2D antigen, which comprise an antibody of the present invention that specifically recognizes human BST2D, or a fragment comprising the antigen-binding domain thereof. Alternatively, the present invention relates to the use of antibodies of the present invention that specifically recognize human BST2D, or fragments comprising the antigen-binding domain thereof, in producing diagnostic agents for detecting tissues expressing a human BST2D antigen. The present invention further relates to the use of antibodies of the present invention that specifically recognize human BST2D, or fragments comprising the antigen-binding domain thereof, in diagnosis to detect tissues expressing a human BST2D antigen.

In the present invention, tissues expressing human BST2D antigen include, for example, tumors expressing a human BST2D antigen. Tumors derived from cells of bone marrow, more specifically myeloma, have been demonstrated to express human BST2D antigen at high levels. The type of myeloma particularly preferred as a target of diagnosis in the present invention is multiple myeloma.

Antibodies of the present invention that specifically recognize human BST2D, or fragments comprising the antigen-binding domain thereof can be used for in vitro or in vivo diagnosis. For example, cells or tissues expressing human BST2D antigen such as myeloma can be identified in vitro from samples collected from patients. Biological tissues used in such diagnosis include bone marrow tissues. Alternatively, localization of cells or tissues expressing human BST2D antigen in a living body can be identified by administering to a patient an antibody that specifically recognizes human BST2D and monitoring the accumulation of the antibody.

Methods for detecting the in vitro binding of antibodies to cells or tissues are known. For example, when antibodies are labeled with a fluorescent dye or enzyme in advance, their binding to fixed samples can be monitored using the label as an indicator. Alternatively, antibodies can be indirectly labeled using the avidin-biotin system. It is possible to use in vivo methods for monitoring the presence of antibodies in a living body using radionuclide-labeled antibodies. For example, methods of image diagnosis using tumor antigen-recognizing antibodies labeled with radionuclides such as technetium 99m ($^{99m}$Tc) have been put to practical use for diagnosing tumor tissues in the body. Antibodies and fragments comprising the antigen-binding domain thereof can be directly labeled with $^{99m}$Tc by reduction. Radionuclides administered to a body can be visualized as an image by using scintillation cameras or single photon CT (SPECT) devices. The localization of tumor tissues expressing human BST2D can be determined by applying such methods to the present invention. More specifically, such methods can be used to diagnose primary and metastatic foci.

For example, tissues expressing BST2 in a living body can be detected by scintigraphy. In this method, an antibody of the present invention that specifically recognizes human BST2D, or a fragment comprising the antigen-binding domain thereof is labeled with $^{99m}$Tc or the like. The labeled antibody or antibody fragment is administered to a patient and $^{99m}$Tc radiation is monitored from outside the body. Such labeled antibodies and fragments can also be used to select appropriate patients for the administration of an antibody of the present invention that specifically recognizes human BST2D, or a fragment comprising the antigen-binding domain thereof by detecting the expression of human BST2D antigen in tumors.

The monoclonal antibodies of the present invention specifically recognize cells and tissues expressing human BST2D. Thus, cells and tissues expressing human BST2D, such as myeloma, can be specifically identified in vitro. Likewise, cells and tissues expressing human BST2D can be detected selectively in vivo. BST2 also includes variants like BST2H, which are demonstrated to be expressed in cells other than myeloma. Thus, background noises and non-specific signals in particular can be excluded in vivo by using BST2D-sepcific antibodies.

All prior art documents cited herein are incorporated herein by reference.

Hereinbelow, the present invention will be specifically described with reference to the Examples, but it is not to be construed as being limited thereto.

EXAMPLES

Example 1

Preparation of Hybridomas Producing Mouse Anti-Human BST2 Antibody

A. Preparation of Immunogen

Cells to be used as an immunogen were prepared by introducing the human BST2D gene into 293T cells by the following method. Four µg of the expression vector pcDNA3.1-hBST2D carrying the gene as an insert was added to a 100-mm Collagen Coated Dish (IWAKI), and mixed with 3 ml of opti-MEM (GIBCO) covering the entire bottom surface of the dish. Then, separately from the solution of expression vector, 58 µl of Lipofectamine™2000 (Invitrogen) was diluted with 3 ml of opti-MEM to prepare lipofectamine solution. The resulting solution was allowed to stand at room temperature for five minutes. Then, the lipofectamine solution was gently added to the dish containing the expression vector solution. The combined solution was mixed and allowed to stand at room temperature for 20 minutes. Ten ml of 293T cells diluted at $1\times10^6$ cells/ml with DMEM (SIGMA) containing 10% FBS (fetal bovine serum) was gently added to the dish. After the cells were incubated in a $CO_2$ incubator at 37° C. for 48 hours, they were collected by pipetting. The cells were used as a transfectant for immunization.

B. Hybridoma Preparation (B-1) Immunization

The day before immunization with 293T cells introduced with the human BST2D gene, 200 µl each of PBS and adjuvant (complete adjuvant (FREUND); Mitsubishi Kagaku Iatron, RM606-1) were combined together, and 50-µl aliquots of the resulting emulsion were injected into the soles of each of four female Balb/c mice (four weeks old) for immunization. On the following day, $2\times10^7$ cells were suspended in 400 µl of PBS, and a 50-µl aliquot of the suspension was injected into each of the mice for immunization. The second and third immunizations were given at three-day intervals, and three days after the third immunization, cell fusion was carried out by the following procedure.

(B-2) Cell Fusion

Cells were collected from the lymph nodes of both legs of each immunized mouse. Cells of the mouse myeloma line P3-X63-Ag8-U1 cultured in RPMI1640 (SIGMA) containing 10% FBS were combined with the mouse lymph node cells at a ratio of 2:1 to 10:1. The combined cells were collected by centrifugation. PEG4000 (MERCK) diluted with an equal volume of RPMI1640 was added to the obtained cell fraction to perform cell fusion. After washing, the cells were suspended in 160 ml of 15% FBS-HAT containing supplements and plated in sixteen 96-well plates at 200 µl/well. The medium was changed after three days. The primary screening was carried out one to two weeks after colony formation was confirmed.

C. Primary Hybridoma Screening by Cell ELISA Method

Primary screening for antibody-producing hybridomas of interest was carried out using the cell ELISA method by the following procedure. $1 \times 10^7$ cells prepared as described in A of Example 1 were suspended in 10 ml of 0.5% BSA/2 mM EDTA/PBS, and aliquoted into cell ELISA plates (NUNC 249570 96V NW PS) at 100 µl/well. The plates were centrifuged at 2000 rpm for two minutes. After the supernatants were removed, the hybridoma culture supernatants were added at 50 µl/well. The plates were incubated at room temperature for 30 minutes. After two rounds of washing (0.5% BSA/2 mM EDTA/PBS), 50 µl of 10000× diluted peroxidase-labeled goat anti-mouse IgG antibody (MBL; Code330) was added to the wells. The plates were incubated for 30 minutes. After three rounds of washing, a chromogenic solution was added, and OD 450 nm-620 nm was measured for selection of positive wells.

D. Assessment of Antibody Binding Activity by Flow Cytometry (FMC) Analysis

The hybridoma culture supernatants were analyzed by flow cytometry (FCM). The cells prepared as described in A of Example 1 were suspended in 0.5% BSA/2 mM EDTA/PBS, and collected into centrifuge tubes at $1 \times 10^5$ cells/sample. 40 µl of each hybridoma culture supernatant was added, and the tubes were incubated at room temperature for 30 minutes. Then, a 1-ml aliquot of 0.5% BSA/2 mM EDTA/PBS was added to each tube, the tubes were centrifuged for three minutes at 1200 rpm and 4° C., and the supernatants were discarded; this washing process was repeated twice. A 40-µl aliquot of 100× diluted FITC-labeled goat anti-mouse IgG antibody (Beckman coulter; IM0819) was added to each tube after washing. The tubes were incubated at room temperature for 30 minutes. Following two rounds of washing, the hybridoma culture supernatants were analyzed with flow cytometer FC500 (Beckman coulter) to assess whether the antibody in the supernatants could specifically recognize human BST2D. Hybridomas producing antibodies that specifically bind to 293T cells expressing human BST2D but are incapable of binding to 293T cells that do not express human BST2D were selected by the FCM analysis. The selected hybridomas were cloned by the limiting dilution method. The resulting hybridomas producing mouse anti-human BST2 antibody were named #3LD, #4LD, #7LD, #9LD, and #19LD.

Example 2

Preparation of Mouse Anti-Human BST2 Monoclonal Antibodies and their Specificity Assessment A. Hybridoma Culture Hybridomas #3LD, #4LD, #7LD, #9LD, and #19LD as prepared in Example 1, which produce mouse anti-human BST2 antibody, were each cultured in RPMI supplemented with 5% FBS. The composition of the culture medium is shown below. The culture temperature and period were 37° C. and 96 hours, respectively.

RPMI supplemented with 5% FBS:
RPMI1640 (Sigma; catalog No. R8758)
5% FBS
0.01 M HEPES
1 mM Sodium pyruvate
2 mM L-Glutamine
100 U/ml Penicillin
100 µg/ml Streptomycin
55 µM 2-Mercptoethanol
pH 7.2 to 7.4

After 96 hours of culture, the culture supernatant of each hybridoma was collected and cell debris was removed by centrifugation. The resulting supernatant was used as a crude antibody solution.

B. Antibody Purification

The crude antibody solutions prepared as described in A were each purified using Protein A affinity column (rProtein A Sepharose FF; Amersham Pharmacia, catalog No. 17-1279-01). The purification conditions are described below. Affinity purification was performed according to the instruction manual appended to the column using PBS(-) buffer as the adsorption buffer and 0.1 M sodium citrate buffer (pH 3) as the elution buffer. The composition of PBS (-) is shown below. The eluted fractions were adjusted to pH of about 7.2 by adding 1 M Tris-HCl (pH 8.0). The buffer of each antibody solution prepared was replaced with PBS(-) using dialysis membrane (cut off 10000; PIERCE). Purified mouse anti-human BST2 monoclonal antibodies #3LD, #4LD, #7LD, #9LD, and #19LD (hereinafter abbreviated as "mouse antibody #3LD", "mouse antibody #4LD", etc.) were obtained. The concentrations of the purified antibodies were determined by absorbance measurement at 280 nm and calculation based on the conversion of 1.38 OD into 1 mg/ml.

PBS(-) buffer:
0.2 g/l Monopotassium dihydrogen phosphate
0.2 g/l Potassium chloride
8 g/l Sodium chloride
1.15 g/l Anhydrous disodium monohydrogen phosphate C. Assessment of Antibody Specificity (C-1) Preparation of Target Cell Line (BST2D-CHO Cell Line)

On the day before vector introduction, CHO-K1 cells were plated in 6-cm dishes at $6 \times 10^5$ cells/dish. An expression vector carrying the human BST2D gene was introduced into the cells using Effectene Transfection Reagent (QIAGEN). The cells were treated with 800 µg/ml Zeocin (Invitrogen) to select zeocin-resistant lines introduced with the vector.

Human BST2D expression vector introduced: pcDNA3.1-hBST2D; 2 µg.

Then, a cell line expressing high level of BST2D (BST2D-CHO cell line) was obtained using a cell sorter (BD FACSAria (Becton Dickinson)). The selected cell line was confirmed to express high level of BST2D by FCM analysis. The FCM analysis was carried out by the procedure described in D of Example 1, except for the use of BD FACSCaliber (BD) in FCM. The following antibody was used in this analysis.

Antibody used in the FCM analysis: 488-conjugated rat anti-human BST2-5C11 antibody (the anti-human BST2-5C11 antibody is described in WO 2006/013923)

(C-2) Preparation of Target Cell Line (BST2H-CHO Line)

A cell line expressing high level of BST2H (BST2H-CHO cell line) was obtained by the same procedure described in (C-1), except for the introduction of a human BST2H expression vector (pcDNA3.1-hBST2H). The following antibody was used in FCM analysis.

Antibody used in the FCM analysis: 488-conjugated rat anti-human BST2-3D3 antibody (the anti-human BST2-3D3 antibody is an antibody produced by hybridoma deposited under accession No. FERM BP-10339, and is described in WO 2006/013923)

Figure 2:
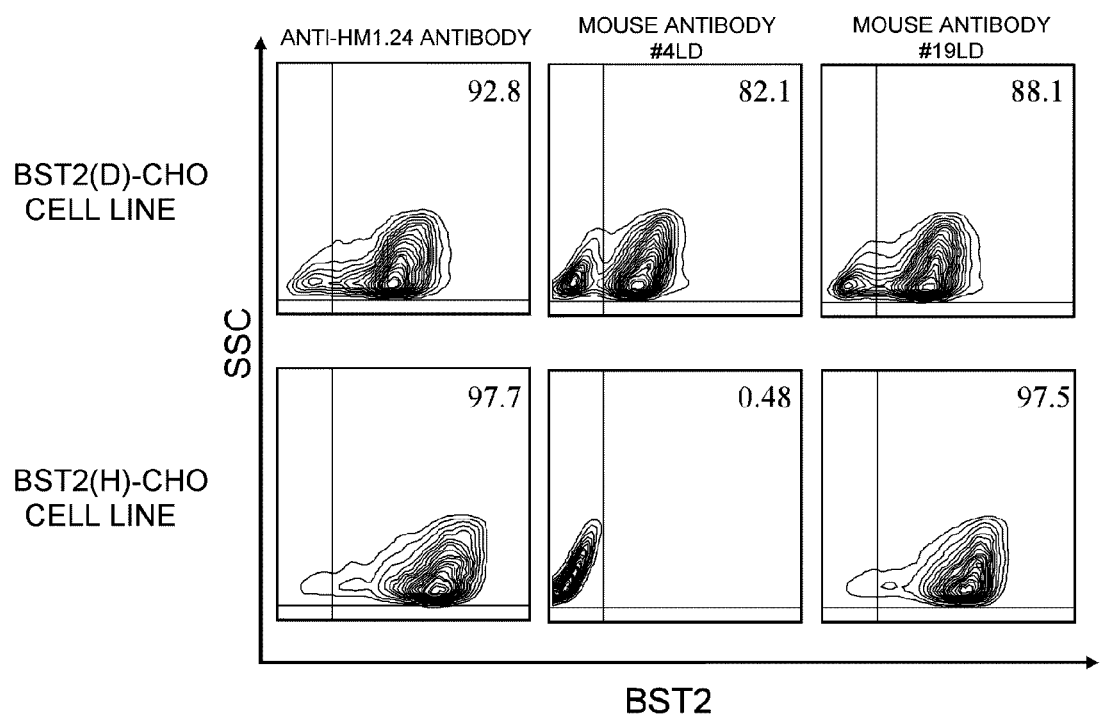
FIG. 2 shows an assessment of the specificity of human BST2 antibodies. CHO cell lines with forced expression of two splicing variants of human BST2 protein, BST2(D) and BST2(H), were prepared and assessed for the binding of anti-HM1.24 antibody and mouse antibodies #4LD and #19LD by flow cytometry. This figure shows the assay result.

(C-3) Assessment of the Binding Specificity of Purified Mouse Anti-Human BST2 Monoclonal Antibodies The five types of purified mouse anti-human BST2 monoclonal antibodies obtained as described above in B were assessed for their binding specificity using the BST2D-CHO cell line prepared as described in (C-1) and the BST2H-CHO cell line prepared as described in (C-2). The assessment was carried out by FCM analysis according to a conventional method. The result of FCM analysis showed that mouse antibodies #3LD, #4LD, and #9LD bound to BST2D-CHO cells but not to BST2H-CHO cells. Mouse antibodies #7LD and #19LD were revealed to bind to both BST2D-CHO and BST2H-CHO cells. Accordingly, in the subsequent experiments, mouse antibodies #3LD, #4LD, and #9LD were treated as antibodies that bind to type D BST2 alone (hereinafter referred to as "anti-human BST2(D+/H−) antibody"), while mouse antibodies #7LD and #19LD were treated as antibodies that bind to both type D and type H BST2 (hereinafter referred to as "anti-human BST2(D+/H+) antibody"). An example of the result obtained by FCM analysis of mouse antibodies #4LD and #19LD is shown in FIG. 2.

(C-4) Assessment of the Reactivity of Mouse Anti-Human HM1.24 Antibody

Anti-HM1.24 antibody (Chugai Pharmaceutical Co. Ltd.), which is a mouse anti-human BST2 antibody, was assessed for its binding specificity by FCM analysis using the same method described in (C-3). The result of FCM analysis is shown in FIG. 2, along with the result of (C-3). The mouse anti-human HM1.24 antibody was also reconfirmed to be an antibody that binds to both BST2D-CHO and BST2H-CHO cell lines.

Example 3

CDC and ADCC Assays of Anti-Human BST2(D+/H−) Antibody

A. Antibody

Using mouse antibody #4LD prepared as described in Example 2, CDC assay was carried out by the method described below.

B. CDC Assay (B-1) Target Cell Lines

The following cells were used as target cell lines.

BST2D-CHO cell line: prepared by the same procedure as described in (C-1) of Example 2

BST2H-CHO cell line: prepared by the same procedure as described in (C-2) of Example 2 Human myeloma-derived cell line RPMI8226

(B-2) Reaction of Target Cells with Anti-Human BST2(D+/H−) Antibody

BST2D-CHO and BST2H-CHO cells described above in (B-1) were harvested using a solution of 5 mM EDTA/PBS, and then suspended at $4 \times 10^5$ cells/ml in CDC medium. The composition of the medium is shown below. RPMI8226 cells derived from human myeloma were also suspended at $4 \times 10^5$ cells/ml in CDC medium. These suspensions were aliquoted into round-bottomed 96-well plates at 50 μl/well.

CDC Medium:
RPMI1640
0.1% BSA
100 units/ml Penicillin
100 μg/ml Streptomycin
10 mM Hepes (pH 7.6)
2 mM L-Glutamine Anti-BST2(D+/H−) antibody solutions (solutions of mouse antibody #4LD) were prepared at a final antibody concentration of 0.01 μg/ml, 0.1 μg/ml, 1 μg/ml, or 10 μg/ml using CDC medium. 50-μl aliquots of the solutions were added to the cells. After mixing, 50 μl of complement-containing CDC medium was added to the cells at a final complement concentration of 6%. The composition of the medium is shown below. The resulting mixtures were incubated at 37° C. for two hours. Samples containing mouse IgG2a, instead of the anti-BST2(D+/H−) antibody, were also prepared and used as a control. CDC assay using anti-HM1.24 antibody, an anti-BST(D+/H+) antibody, was also carried out at the same time as a control for comparison with mouse antibody #4LD.

Complement-Containing CDC Medium:
1 ml Baby rabbit complement (CEDARLANE, catalog No. CL3441)
CDC medium (described above)

Then, the round-bottomed 96-well plates containing the suspensions were centrifuged (conditions of centrifugation: 250 G for four minutes). The culture supernatants were collected with caution so as not to contaminate the cells. The levels of LDH in the culture supernatants were determined using CytoTox96™ Assay (PROMEGA). The LDH level was defined as the "amount of LDH leakage from target cells as a result of complement activity (Experimental Sample)".

The parameters described below were also used to determine CDC:

Amount of LDH spontaneously released from target cells (Target Cell Spontaneous LDH Release): prepared by culturing the same volume of target cells alone as the samples.

Amount of maximum LDH release from target cells (Target Cell Maximum LDH Release): prepared by culturing the same volume of target cells alone as the samples. Sixty minutes before collecting the supernatant, the TritonX-100 solution attached to the kit was added at a final concentration of 0.8%.

Control for liquid volume normalization (Volume Correction Control): prepared by adding the same volume of TritonX-100 as in the preparation of "Target Cell Maximum LDH Release" to the same volume of culture medium as the sample. "Volume Correction Control" is referred to as "Volume Control" in the CDC (%) calculation formula shown below.

A control for the background level in culture medium (Culture Medium Background): a solution of the same volume as the samples was prepared by adding complement-containing CDC medium to a culture medium of the same volume as the samples.

The absorbance of each of Target Maximum and Target Spontaneous was normalized by subtracting the absorbance of the same-sample-volume medium. The absorbance of Experimental Sample was normalized by subtracting the absorbance of the same-sample-volume solution prepared by adding complement-containing CDC medium to the medium.

CDC was calculated from each of the determined LDH levels according to the following formula.

$$\text{CDC}(\%) = [(\text{Experimental Sample}) - (\text{Target Spontaneous})] / [(\text{Target Maximum}) - (\text{Volume Control}) - (\text{Target Spontaneous})] \times 100 \quad \text{Formula 1:}$$

Figure 3:
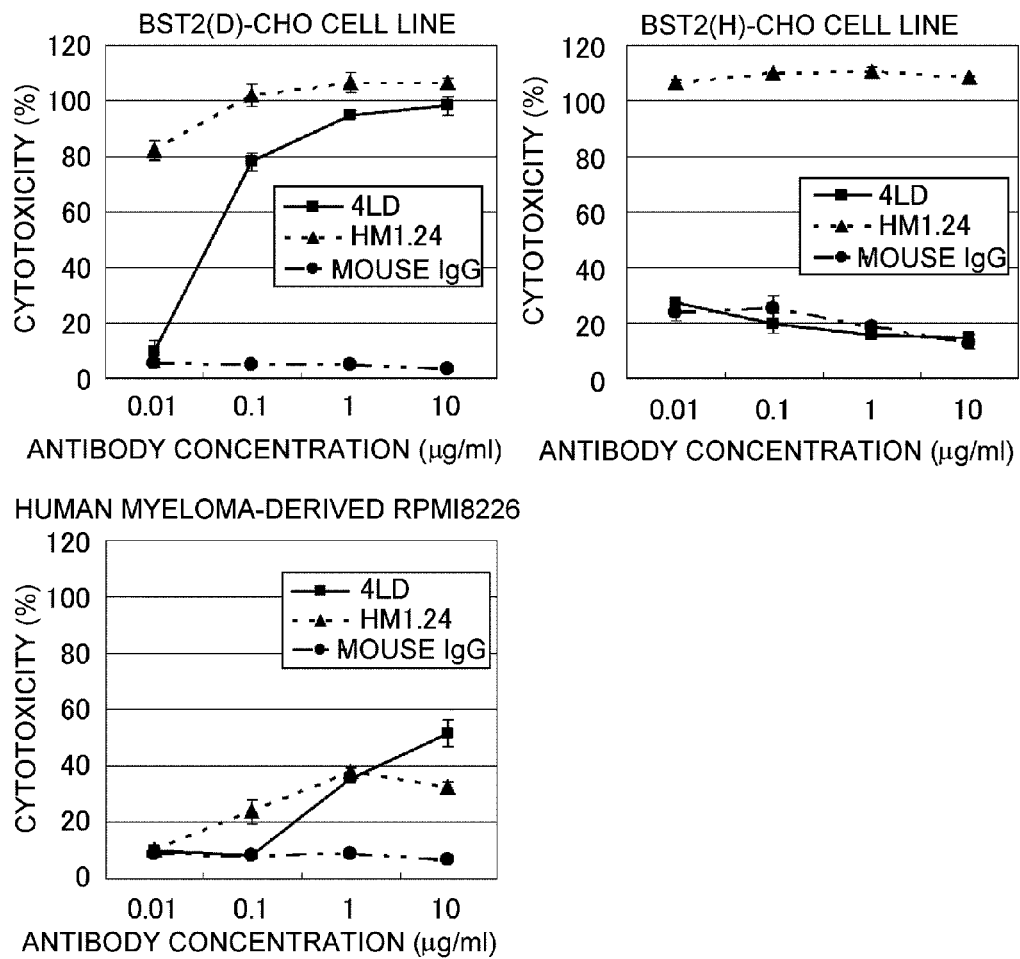
FIG. 3 presents graphs showing results of CDC assay of anti-HM1.24 antibody and mouse antibody #4LD against BST2-expressing cells. CDC was assessed using BST2(D)-CHO, BST2(H)-CHO, and human myeloma-derived RPMI8226. The amount of LDH released to the culture medium during a two-hour incubation of the cells with 0.01-10 μg/ml antibody at 37° C. in the presence of rabbit complements was determined as cytotoxicity (%).

The result is shown in FIG. 3. Mouse antibody #4LD (anti-human BST2(D+/H−) antibody) had almost no CDC against BST2(H)—CHO cells, but in contrast showed strong CDC against BST2(D)-CHO cells.

C. ADCC Assay (C-1) Target Cell Lines and Effector Cells

The target cell lines used are as follows:

BST2D-CHO cell line: prepared by the same procedure as described in (C-1) of Example 2

Human myeloma-derived cell line RPMI8226

The effector cells used are as follows:

Human peripheral mononuclear cells: peripheral mononuclear cells isolated from human peripheral blood by the Ficoll method were used.

(C-2) Reaction of Target Cells, Anti-Human BST2(D) Antibody, and Effector Cells

BST2D-CHO cells and human myeloma-derived RPMI8226 cells described above in (B-1) were harvested using a solution of 5 mM EDTA/PBS, and suspended at $4 \times 10^5$ cells/ml in RPMI containing 10% FBS. These suspensions were aliquoted into round-bottomed 96-well plates at 50 µl/well.

An anti-BST2 antibody solution was prepared at a final antibody concentration of 10 µg/ml using RPMI containing 10% FBS. 50 µl of the antibody solution was added to the cells. After mixing, the cells were incubated at 4° C. for 30 minutes. Then, effector cells were combined in an amount 25, 50, or 100 times of that of the target cells, and 50 µl each of the cell mixtures were added to the plates. After mixing, the plates were centrifuged (conditions of centrifugation: 250 G for four minutes) to bring the target and effector cells closer. Then, the cells were incubated at 37° C. for four hours. Anti-BST2 antibodies used were: mouse antibody #4LD (anti-human BST2(D+/H−) antibody), chimeric #4LD antibody (chimeric anti-human BST2(D+/H−) antibody; see Examples 5 and 6), mouse anti-HM1.24 antibody, and humanized anti-HM1.24 antibody (Patent Document 3, WO 2002/064159; Patent Document 4, WO 2005/034994). In this experiment, samples were prepared using mouse IgG2a instead of an anti-BST2 antibody, and used as controls.

Then, the suspensions were centrifuged (conditions of centrifugation: 250 G for four minutes). The culture supernatants were collected with caution so as not to contaminate the cells. The levels of LDH in the culture supernatants were determined by a conventional method. The LDH level was defined as the "amount of LDH leakage from target cells as a result of cytotoxic activity (Experimental Sample)".

The parameters described below, which are similar to those described in (B-2), were also used to determine ADCC:

Amount of LDH spontaneously released from target cells (Target Cell Spontaneous LDH Release): prepared by culturing the same volume of target cells alone as the samples.

Amount of maximum LDH release from target cells (Target Cell Maximum LDH Release): prepared by culturing alone the same volume of target cells as the samples. Sixty minutes before collecting the supernatant, the solution of TritonX-100 attached to the kit was added at a final concentration of 0.8%.

Amount of LDH spontaneously released from effector cells (Effector Cell Spontaneous LDH Release): prepared by culturing the same volume of effector cells alone as the samples.

Control for liquid volume normalization (Volume Correction Control): prepared by adding the same volume of TritonX-100 as in the preparation of "Target Cell Maximum LDH Release" to the same volume of culture medium as the samples. "Volume Correction Control" is referred to as "Volume Control" in the ADCC (%) calculation formula shown below.

A control for the background level in culture medium (Culture Medium Background): a medium of the same volume as the samples was prepared.

The absorbance of each of Target Spontaneous, Target Maximum, Effector Spontaneous, and Experimental Sample was normalized by subtracting the absorbance of Culture Medium Background.

ADCC was calculated according to the following formula.

Figure 4:
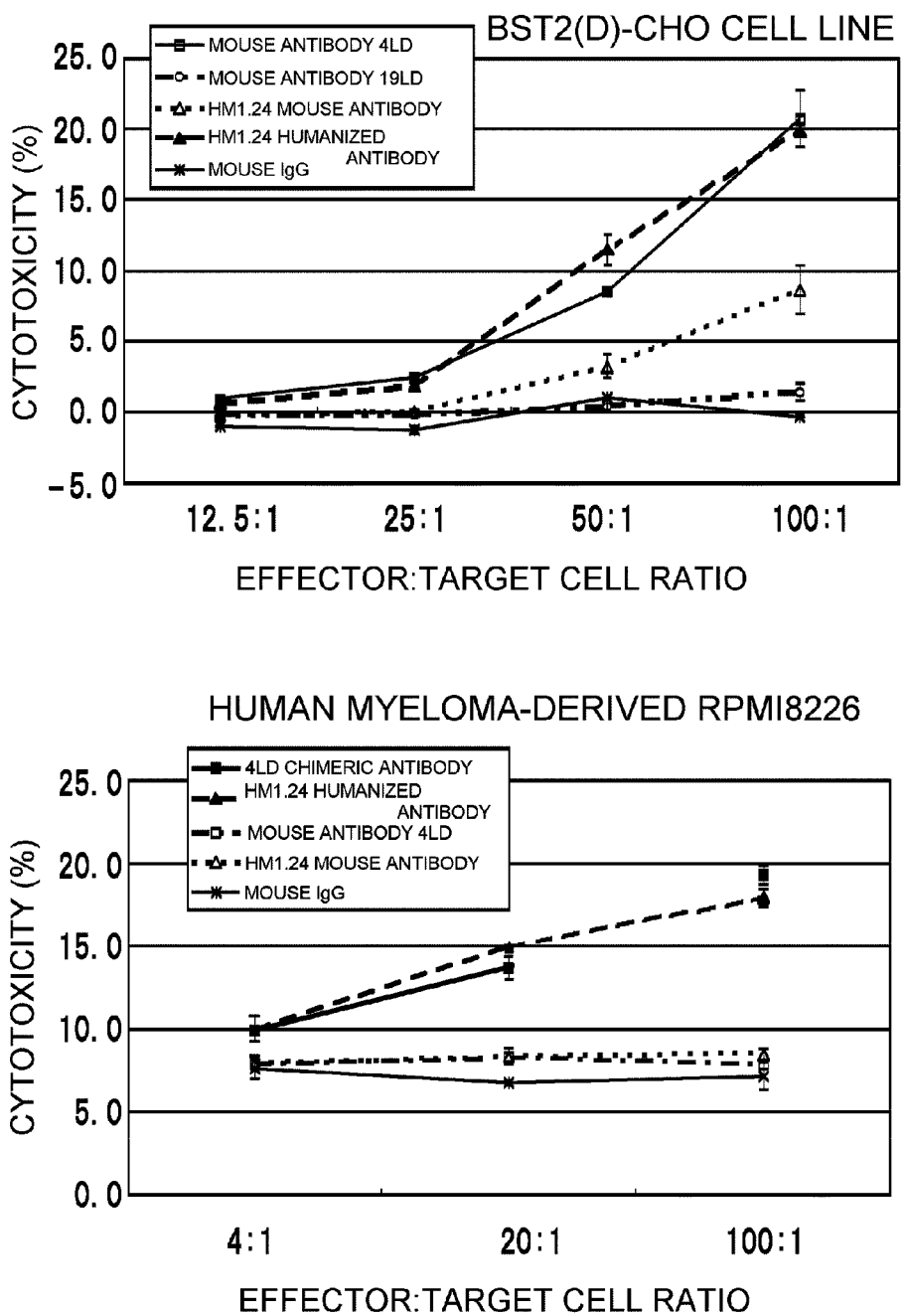
FIG. 4 presents graphs showing results of ADCC assay of anti-HM1.24 antibody, mouse antibody #4LD, chimeric #4LD, and mouse antibody #19LD against BST2-expressing cells. The target cells used in this ADCC assay were BST2 (D)-CHO and RPMI8226 cells, and the effector cells were human PBMC. The amount of LDH leakage to the supernatant as a result of cell killing within an E/T ratio of 12.5 to 100 was determined as ADCC (%). The humanized anti-HM1.24 antibody (AHM antibody) was used as a control.

ADCC(%)=[(Experimental Sample)−(Target Spontaneous)−(Effector Spontaneous)]/[(Target Maximum)−(Volume Control)−(Target Spontaneous)]×100    Formula 2:

The result is shown in FIG. 4. Mouse antibody #4LD showed strong ADCC against BST2D-CHO cells. The activity was comparable to that of humanized anti-HM1.24 antibody. On the other hand, mouse antibody #4LD exhibited almost no ADCC against PRMI8266 cells. In contrast, chimeric #4LD antibody showed strong ADCC against the cells, and the activity was revealed to be comparable to that of humanized anti-HM1.24 antibody.

Comparative Example 1

CDC of Anti-human BST2(D+/H+) Antibody

CDC assay was carried out using mouse anti-human HM1.24 antibody by the same method described in Example 3.

The result is shown in FIG. 3, which also includes the result of Example 3. Mouse anti-human HM1.24 antibody (anti-human BST2(D+/H+) antibody) exhibited strong CDC against both BST2(H)-CHO and BST2(D)-CHO cells, and the activity was comparable between these two types of cells. Mouse anti-human BST2 #4LD antibody (anti-human BST2 (D+/H−) showed CDC specific to BST2(D)-CHO cells but did not exhibit cell-killing effect in BST2(H)—CHO cells.

Example 4

Binding of Anti-Human BST2(D+/H−) Antibody to Various Biological Tissues

A. Binding to Human and Cynomolgus Monkey Peripheral Blood Mononuclear Cell Fractions (Hereinafter Referred to as "PBMC")

PBMCs were stained with mouse antibody #4LD labeled with an PE-labeled goat anti-mouse antibody, and analyzed by flow cytometry using a conventional method. Reagents and devices used are listed below.

Flow cytometry (FACSCalibur, etc.) (Becton Dickinson)
Secondary antibody: R-PE-Conjugated Goat Anti-Mouse Immunoglobulin Specific
Polyclonal Antibody (Multiple Adsorption) (BD Biosciences: 550589)
HISTOPAQUE-1077 (SIGMA H8889)
FcR Blocking Reagent (Milteny Biotec 130-059-901)
RPMI1640 containing 5% FCS, penicillin-streptomycin, and L-glutamine
ACK Lysis solution (0.15M $NH_4Cl$, 10 mM $KHCO_3$, 0.1 mM $Na_2EDTA$, pH 7.2 to 7.4)

Blood was diluted with RPMI1640 (without FCS), overlaid on HISTOPAQUE-1077, and then centrifuged at 1800 rpm for 20 minutes. The middle layer was collected and RPMI1640 was added thereto. The resulting suspension was centrifuged at 1800 rpm for ten minutes. The supernatant was aspirated, and 1 ml of ACK Lysis solution was added to the cell pellet. After the resulting suspension was allowed to stand on ice for three minutes, RPMI1640 was added thereto, and the suspension was centrifuged at 1200 rpm for five minutes. The supernatant was aspirated, and RPMI1640 was added to the cell pellet to suspend the PBMCs. The cells were counted and then centrifuged at 1200 rpm for five minutes. Using 20% FCR blocking reagent/1% FCS/PBS, PBMC suspension was prepared at $5\times10^7$ cells/ml, and a 10-μl aliquot ($5\times10^5$ cells) was added to each well of round-bottomed 96-well plates. Then, 25 μl of 1 μg/ml mouse antibody #4LD was added to each well. After the plates were allowed to stand at 4° C. in the dark for 15 minutes, 150 μl of PBS containing 1% FCS was added thereto. The plates were centrifuged at 2000 rpm for two minutes. After the resulting supernatants were discarded, PBS containing 1% FCS was added and the plates were centrifuged at 2000 rpm for two minutes. The resulting supernatants were discarded. 20 μl of the secondary antibody was added to each well. After the plates were allowed to stand at 4° C. in the dark for 15 minutes, 150 μl of PBS containing 1% FCS was added thereto. The plates were centrifuged at 2000 rpm for two minutes and the resulting supernatants were discarded. The cells were suspended in 150 μl of PBS containing 1% FCS. The plates were centrifuged at 2000 rpm for two minutes and the resulting supernatants were discarded. The cells were suspended in 150 μl of PBS containing 1% FCS and transferred to FACS tubes. Then, 150 μl of PBS containing 1% FCS was added to the tubes. Following analysis with FACSCalibur, the percentage of staining PBMCs was determined using FlowJo software. The result is shown in Table 1.

B. Histochemical Staining of Frozen Sections of Human Splenic Tissue

Figure 5:
FIG. 5 presents photographs showing frozen sections of human spleen tissues immunostained with antibody #4LD or #19LD.

Frozen sections of human splenic tissue were stained with mouse antibody #4LD labeled with a polymer reagent (DAKO K5007) according to a conventional method. Micrographs of the tissue are shown in FIG. 5. Mouse antibody #4LD hardly bound to the human splenic tissue. In contrast, mouse antibody #19LD described in Comparative Example bound well to the human splenic tissue. This result demonstrates that mouse antibody #4LD is more specific than mouse antibody #19LD.

C. Binding to Myeloma-Derived RPMI8226 Cells

RPMI8226 cells were stained with mouse antibody #4LD, mouse antibody #19LD, and anti-HM1.24 antibody at concentrations of 0.01, 0.1, 1, and 10 μg/ml. Using Prism 4 software, the equilibrium-dissociation constants (Kd) were calculated based on the determined percentage of staining.

Reagents and devices used are listed below.

Prism 4 software (GraphPad Software, Inc.)
FlowJo software (Tree Star, Inc.)
Flow cytometry (FACSCalibur, etc.) (Becton Dickinson)
Secondary antibody: mouse Ig-FITC (Fluorescein Isothiocyanate-Conjugated Goat Anti-Mouse Immunoglobulin Specific Polyclonal Antibody (Multiple Adsorption); BD Biosciences: 554001), etc.

The cells were collected and counted, and then suspended at $1\times10^6$ cells/ml in PBS containing 1% FCS. The suspension was added to 96-well v-bottomed plates at 100 μl/well ($1\times10^5$ cells/well). The plates were centrifuged at 2000 rpm for two minutes, and the resulting supernatants were discarded. A 25-μl aliquot of 0.01, 0.1, 1, or 10 μg/ml mouse antibody #4LD, mouse antibody #19LD, or anti-HM1.24 antibody was added to each well. After the plates were allowed to stand in the dark at 4° C. for 15 minutes, 150 μl of PBS containing 1% FCS was added thereto. The plates were centrifuged at 2000 rpm for two minutes, and the resulting supernatants were discarded. PBS containing 1% FCS was added, and the plates were centrifuged at 2000 rpm for two minutes. The resulting supernatants were discarded. The secondary antibody was added at 20 μl/well. After the plates were allowed to stand in the dark at 4° C. for 15 minutes, 150 μl of PBS containing 1% FCS was added thereto. The plates were centrifuged at 2000 rpm for two minutes, and the resulting supernatants were discarded. 150 μl of PBS containing 1% FCS was added. The plates were centrifuged at 2000 rpm for two minutes, and the resulting supernatants were discarded. The cells were suspended in 150 μl of PBS containing 1% FCS and transferred to FACS tubes. Then, 150 μl of PBS containing 1% FCS was added to the wells for washing and then transferred to the tubes. Following analysis with FACSCalibur, the percentage of staining PBMCs was determined using FlowJo software. Furthermore, using Prism 4 software, the Kd values were calculated based on the determined percentage of staining. The result is shown in Table 2. Mouse antibody #4LD exhibited high affinity for RPMI8226 cells as compared to anti-HM1.24 antibody and mouse antibody #19LD.

Comparative Example 2

Binding of Anti-Human BST2(D+/H+) Antibody to Various Biological Tissues

The same experiment described in Example 4 was carried out using mouse antibody #19LD or anti-HM1.24 antibody instead of mouse antibody #4LD. The result is shown in Tables 1 and 2, and FIG. 5, which also include the result of Example 4.

TABLE 1

Binding of anti-human BST2 antibody to human and cynomolgus monkey PBMCs

| | Example 4 Anti-human BST2(D+/H−) antibody | Comparative Example 2 Anti-human BST2(D+/H+) antibody | |
|---|---|---|---|
| | Mouse antibody #4LD | Mouse antibody #19LD | Anti-HM1.24 antibody |
| Human | 6% | 60% | 99% |
| Cynomolgus monkey | 3% | 85% | 96% |

TABLE 2

Binding activity (Kd value) to human myeloma-derived RPMI8226 cells

| Example 4 Anti-human BST2(D+/H−) antibody | Comparative Example 2 Anti-human BST2(D+/H+) antibody | |
|---|---|---|
| Mouse antibody #4LD | Mouse antibody #19LD | Anti-HM1.24 antibody |
| 0.1 nM | 0.93 nM | 0.24 nM |

It was demonstrated that mouse antibody #4LD, which is an anti-human BST2(D+/H−) antibody, strongly bound to therapeutic target cells such as myeloma cells, but in contrast its binding to non-target cells in the present invention, such as PBMC and HUVEC, was very weak. Accordingly, decrease in the anti-human BST2 antibody level in blood after administration can be prevented when the anti-human BST2(D+/H−) antibody is used as the anti-human BST2 antibody. In this case, the antibody is likely to be supplied at higher concentrations to therapeutic target tissues.

Example 5

Construction of Chimeric Anti-BST2(D+/H−) Antibody (Chimeric #4LD Antibody)

A. Isotyping of Constant Region

Isotyping of the constant region of mouse antibody #4LD produced by the hybridoma was carried out using the culture supernatant and a mouse monoclonal antibody isotyping kit (Serotec Product; catalog No. MMT1) available on the market. The heavy- and light-chain constant regions were found to be Igγ2a and Igκ, respectively.

B. Cloning of cDNA Encoding Variable Region of Mouse Antibody #4LD (B-1) Hybridoma Used in cDNA Cloning The hybridoma used was hybridoma #4LD producing mouse anti-human BST2D antibody.

(B-2) Isolation of Total RNA

Total RNA was isolated from the hybridoma described above in (A-1) using the commercially available "RNeasy Mini Kit" (Qiagen; catalog No. 74106) according to the instruction manual appended to the kit. In each batch, about 200 μg of total RNA was obtained from $1 \times 10^7$ hybridomas.

(B-3) Amplification and Fragmentation of cDNA Encoding Mouse Heavy-Chain Variable Region Complementary DNA encoding mouse heavy-chain variable region was amplified by 5'RACE using a 5-μg aliquot of total RNA isolated as described in (B-2). The amplification was carried out using a commercially available kit, 5' RACE System for Rapid Amplification of cDNA ENDs, Version 2.0 Kit (Invitrogen; catalog No. 18374-058). The procedure is described in detail below. As a first step, the first strand cDNA was synthesized with reverse transcriptase from the total RNA obtained as described in (A-2). The antisense primer (GSP1) used in the first strand synthesis is indicated below (SEQ ID NO: 14). Then, total RNA was digested with RNaseH, and the single-stranded first strand cDNA remained intact was purified using 1.5% low-melting-point agarose. Next, a nucleotide homopolymer of dC was added to the 3' end of the first-strand cDNA using terminal deoxynucleotidyl transferase (TdT). The cDNA was then amplified by PCR using anchor primer (SEQ ID NO: 16) with a nucleotide polymer complementary to dC (anchor sequence) at its 3' end and antisense primer (GSP2) (SEQ ID NO: 15) shown below. Using the resulting PCR product as template, the cDNA was further amplified by nested PCR using AUAP primer (SEQ ID NO: 17) and antisense primer (GSP2) (SEQ ID NO: 15). Then, the PCR product was purified using 1.5% low-melting-point agarose.

```
Mu IgG2aVH5RACE-GSP1
                                       (SEQ ID NO: 14)
5' TCC AGA GTT CCA GGT CAA GGT CAC 3' (24-mer)

Mu IgG2aVH5RACE-GSP2
                                       (SEQ ID NO: 15)
5' GCC AGT GGA TAG ACC GAT GG 3' (20-mer)

5' RACE anchor primer
                                       (SEQ ID NO: 16)
5'-GGC CAC GCG TCG ACT AGT ACG GGI IGG GII GGG
IIG-3' (36-mer)

5' RACE AUAP primer
                                       (SEQ ID NO: 17)
5'-GGC CAC GCG TCG ACT AGT AC-3' (20-mer)
```

(B-4) Amplification and Fragmentation of cDNA Encoding Mouse Light-Chain Variable Region By the same procedure described in (B-3), cDNA encoding mouse light-chain variable region was amplified from total RNA isolated as described in (B-2). In this amplification, the antisense primers used are shown below. The resulting PCR product was purified using 1.5% low-melting-point agarose.

```
Mu IgVL5RACE-GSP1
                                       (SEQ ID NO: 18)
5' TTC ACT GCC ATC AAT CTT CCA CTT 3' (24-mer)

Mu IgVL5RACE-GSP2
                                       (SEQ ID NO: 19)
5' GAT GGA TAC AGT TGG TGC AGC 3' (21-mer)
```

(B-5) Determination of Nucleotide Sequence of cDNA and Identification of CDRs

The cDNA fragments of heavy-chain and light-chain variable regions, which were obtained as described in (B-3) and (B-4), respectively, were each cloned into the pCR4Blunt-TOPO vector using a commercial kit, Zero Blunt TOPO PCR Cloning Kit (Invitrogen; catalog No. 1325137), according to the instruction manual appended to the kit. The resulting vectors were introduced into E. coli competent cells to obtain E. coli transformants. The plasmids described above were isolated from the transformants. The nucleotide sequences of the cDNAs in the plasmids were determined using an automatic DNA sequencer, PCR-based ABI PRISM 3100 Genetic Analyzer (Applied Biosystems). Inactive RNA transcripts as a result of frameshifts, nonsense mutations, or the like near the complementary determining regions (hereinafter referred to as "CDR") were excluded and transcripts with the correct sequences were extracted. Furthermore, homology search of the cDNA nucleotide sequences in the plasmids against the Kabat Database was performed to identify the CDRs of the variable regions and the sequences of the respective variable regions.

The nucleotide sequence of the heavy-chain variable region of mouse antibody #4LD obtained as described in (B-3) is shown in SEQ ID NO: 10, and the amino acid sequence is shown in SEQ ID NO: 11. The amino acid sequences of CDR1, CDR2, and CDR3 in the heavy-chain variable region of mouse antibody #4LD are shown in SEQ ID NOs: 4, 5, and 6, respectively.

The nucleotide sequence of the light-chain variable region of mouse antibody #4LD obtained as described in (B-4) is shown in SEQ ID NO: 12, and the amino acid sequence is shown in SEQ ID NO: 13. The amino acid sequences of CDR1, CDR2, and CDR3 in the light-chain variable region of mouse antibody #4LD are shown in SEQ ID NOs: 7, 8, and 9, respectively.

C. Cloning of cDNA Encoding Human IgG Constant Region

Human IgG1 heavy-chain constant region and human Ig kappa light-chain constant region were selected from a cDNA library of cells producing human interferon (Interferon Producing cells; IPC). The cDNAs were each cloned into the pCR4Blunt-TOPO vector using a commercial kit, Zero Blunt TOPO PCR Cloning Kit (Invitrogen; catalog No. 1325137), according to the instruction manual appended to the kit. The resulting vectors were introduced into E. coli competent cells to obtain E. coli transformants. The plasmids were isolated from the transformants. The nucleotide sequences of the cDNAs in the plasmids were determined using an automatic DNA sequencer, PCR-based ABI PRISM 3100 Genetic Analyzer (Applied Biosystems).

D. Ligation of Variable and Constant Regions and Cloning

The mouse antibody #4LD heavy-chain variable region obtained as described in (B-5) and the human IgG heavy-chain constant region obtained as described in C shared an overlapping DNA sequence. Thus, double-stranded DNA was obtained using this region by the overlap extension method. The procedure is described in detail below.

(D-1) Construction of cDNA Encoding the Heavy Chain of Chimeric #4LD Antibody

The "plasmid carrying cDNA encoding the heavy-chain variable region of mouse antibody #4LD" obtained as described in (B-5) was digested with restriction enzymes NotI and XbaI, and purified using 1.5% agarose gel. The DNA was dissolved at 100 pmol/μl in TE buffer to prepare a solution of cDNA fragment encoding the heavy-chain variable region of mouse antibody #4LD. The composition of the TE buffer is indicated below.

TE buffer:
10 mM Tris-HCl
1 mM EDTA
pH 7.5 to 8.0

Furthermore, the "plasmid carrying cDNA encoding the heavy-chain constant region of human IgG" obtained as described in C was treated by the same procedure. This yielded a solution of 100 pmol/μl cDNA. Then, the two cDNAs were combined together, and incubated at 70° C. for ten minutes and then at 37° C. for five minutes to form hydrogen bonds in the overlapping region. After amplification by PCR, the resulting cDNA was treated with restriction enzymes NotI and XbaI, and purified using 1.5% low-melting-point agarose.

The respective primers used in PCR amplification to construct expression vectors for the heavy and light chains of chimeric #4LD antibody are listed below.

PCR primers for the heavy chain of chimeric #4LD antibody

4LD-VH NotI-1F
(SEQ ID NO: 29)
5' AAA GCG GCC GCG CCG CCA CCA TGA AAG TGT TGA

GTC TGT TGT ACC TGT TG 3' (50-mer)

4LD-VH XbaI-2R
(SEQ ID NO: 30)
5' CTA GTC TAG ATG AGG AGA CTG TGA GAG TGG TGC

CTT GGC 3' (39-mer)

4LD-VH-3F
(SEQ ID NO: 31)
5' GTC TCC TCA GCC TCC ACC AAG GGC CCA TCG GTC 3'

(33-mer)

4LD-VH-4R
(SEQ ID NO: 32)
5' TGA TCA TCA TTT ACC CGG AGA CAG GGA GAG GCT

CTT C 3' (37-mer)

PCR primers for the light chain of chimeric #4LD antibody

4LD-VL NotI-1F
(SEQ ID NO: 33)
5' AAA GCG GCC GCG CCG CCA CCA TGG AGA CAG ACA

CAC TCC TGC 3' (42-mer)

4LD-VL XbaI-2R
(SEQ ID NO: 34)
5' CTA GTC TAG ACG TTT TAT TTC CAG CTT GGT CCC

CCC TCC G 3' (40-mer)

4LD-VL-3F
(SEQ ID NO: 35)
5' AAA TAA AAC GAA CTG TGG CTG CAC CAT CTG TCT

TCA TCT TCC C 3' (43-mer)

4LD-VL-4R
(SEQ ID NO: 36)
5' TGA TCA CTA GCA CTC TCC CCT GTT GAA GCT CTT

TGT GAC 3' (39-mer)

(D-2) Preparation of cDNA Encoding the Light Chain of Chimeric #4LD Antibody

A cDNA encoding the light chain of chimeric #4LD antibody was prepared by the same method described in (D-1) from the light-chain variable region of mouse antibody #4LD obtained as described in (B-5) and the human Ig kappa light-chain constant region obtained as described in C.

(D-3) Cloning

The cDNA obtained as described in (D-1) was cloned into plasmid vector pcDNA3.1-zeocin (Invitrogen) at a cloning site between NotI and XbaI to construct an expression vector for the heavy chain of chimeric #4LD antibody. Furthermore, the cDNA obtained as described in (D-2) was cloned into plasmid vector pcDNA3.1-hygromycin (Invitrogen) at a cloning site between NotI and XbaI to construct an expression vector for the light chain of chimeric #4LD antibody. Each vector was named as follows.

Expression vector for the heavy chain of chimeric #4LD antibody: pcDNA-4LDVH

Expression vector for the light chain of chimeric #4LD antibody: pcDNA-4LDVL

E. Expression of Chimeric #4LD Antibody (E-1) Transient Transformation

Using Effective Transfection Kit (Qiagen; catalog No. 301427), 293T cells were co-transfected with 1 μg each of the expression vectors for the heavy chain (pcDNA-4LDVH) and light chain (pcDNA-4LDVL) of chimeric #4LD antibody obtained as described in (D-3). Then, the cells were cultured at 37° C. using DMEM supplemented with 2% Low IgG FBS. The composition of the medium is shown below.

DMEM supplemented with 2% Low IgG FBS:
DMEM (Sigma; catalog No. D5796)
2% Low IgG FBS (HyClone; catalog No. SH30151.03)
2 mM L-Glutamine
100 U/ml Penicillin
100 μg/ml Streptomycin
pH 7.2-7.4

The cells were cultured for 96 hours after vector introduction. The culture supernatants were collected and centrifuged to remove cell debris. The resulting supernatants were used as crude antibody solutions.

F. Antibody Purification

Each of the crude antibody solutions obtained as described in (E-1) was purified using Protein A affinity column (rProtein A Sepharose FF, Amersham Pharmacia; catalog No. 17-1279-01). The conditions of the column purification are described below. The antibodies were affinity-purified according to the instruction manual appended to the column using PBS(−) buffer as an adsorption buffer and 0.1 M sodium citrate buffer (pH 3) as an elution buffer. The composition of the PBS(−) buffer is shown below. The eluted fractions were adjusted to a pH of about 7.2 by adding 1 M Tris-HCl (pH 8.0). The buffer of each antibody solution prepared was replaced with PBS(−) using dialysis membrane (cut off 10000; PIERCE). Purified chimeric #4LD antibody was obtained.

The concentrations of purified antibodies were determined by absorbance measurement at 280 nm and calculation based on the conversion of 1.38 OD into 1 mg/ml.

PBS(−) buffer
- 0.2 g/l Monopotassium dihydrogen phosphate
- 0.2 g/l Potassium chloride
- 8 g/l Sodium chloride
- 1.15 g/l Anhydrous disodium monohydrogen phosphate The respective nucleotide and amino acid sequences of the constructed heavy and light chains of chimeric #4LD antibody are shown in the following SEQ IDs.

| Heavy chain | Light chain |
|---|---|
| SEQ ID NO: 25 (nucleotide sequence) | SEQ ID NO: 27 (nucleotide sequence) |
| SEQ ID NO: 26 (amino acid sequence) | SEQ ID NO: 28 (amino acid sequence) |

Example 6

Determination of Epitope Recognized by Anti-Human BST2(D+) Antibody

A. Construction of Expression Vectors for Human BST2 Proteins and Preparation of Recombinant Human BST2 Proteins A series of cDNAs were synthesized by PCR, encoding a series of partial amino acid sequences of the extracellular domain from positions 47 to 180 in the entire sequence of human BST2D (SEQ ID NO: 2). The series of partial amino acid sequences were designed as N and C terminal truncations prepared by successive single amino acid deletion from each terminus. The method for designing amino acid sequences of interest is described below.

Design of the amino acid sequences for N terminal analysis:

(47)------------------------------(180)
(47)------------------------------(179)
(47)------------------------------(178)
            :
            :
(47)-------------(140)

Design of the amino acid sequences for C terminal analysis:

(47)------------------------------(180)
(48)------------------------------(180)
(49)------------------------------(180)
            :
            :
(140)---------------(180)

PCR was carried out using primers each annealing to either end of the region encoding a target amino acid sequence within the nucleotide sequence of a human BST2D-encoding cDNA (SEQ ID NO: 1). EcoRI and XhoI sites were added to each primer. PCR was carried out using KOD DNA polymerase from Toyobo and a vector inserted with the full length human BST2 cDNA as template. The resulting PCR products were cleaved with EcoRI and XhoI (TaKaRa), electrophoresed on agarose gel, and then purified with MinElute from Qiagen. The purified PCR products were cloned into pET32 (Novagen), a His-tagged expression vector, between EcoRI and XhoI sites. The expression vectors were introduced into E. coli (BL21 (DE3)) for transformation. Human BST2 proteins each having a His tag at its N terminus were prepared from the respective E. coli strains using Overnight Express System (Novagen).

B. Antibody

Using mouse antibody #4LD obtained as described in Example 2, epitopes were determined by the Western blot method described below.

C. Western Blotting

The His-tagged human BST2 proteins (synthesized as described in A) were each dissolved in sample buffer, and heated at 70° C. for ten minutes. The dissolved proteins were fractionated on a 4-20% SDS-PAGE gradient gel (Invitrogen) and transferred onto PVDF membrane (Millipore). The membrane was blocked with BSA and incubated with 1 μg/ml antibody 4LD or 2000× diluted anti-His tag antibody (Novagen). After reaction with an HRP-labeled anti-mouse IgG antibody (Jackson), ECL Detection Reagent (GE Healthcare) was reacted for chemical luminescence, and the His-tagged human BST2 proteins were detected using LAS-1000 from Fuji Film.

Sample Buffer:
- NuPAGE LDS Sample Buffer (4×) (Invitrogen)
- NuPAGE Reducing Agent (10×) (Invitrogen)

The buffer was prepared using sterile distilled water.

Figure 6:
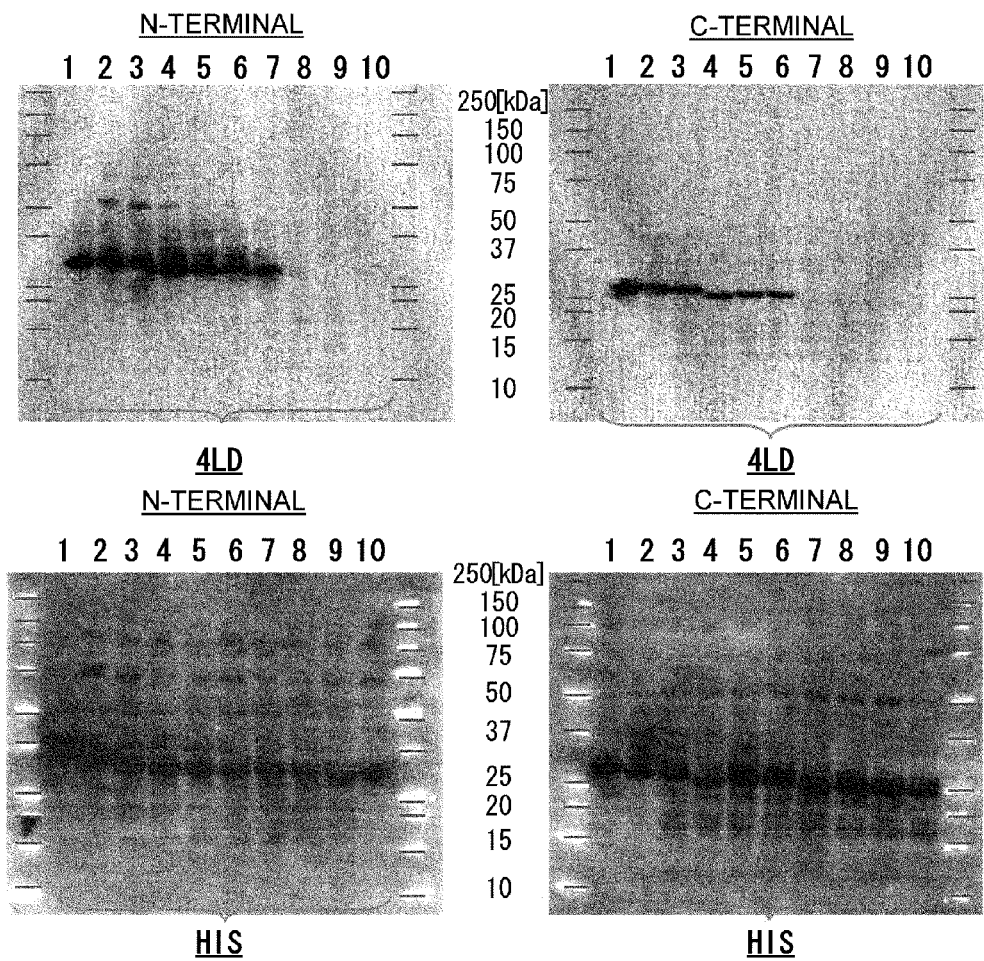
FIG. 6 presents photographs showing result of Western blotting detecting recombinant, His-tagged human BST2 protein using antibody #4LD (upper panels) or anti-His tag antibody (lower panels).

The result is as shown in FIG. 6. The amino acid sequence of recombinant human BST2 protein in each lane is shown below. Amino acid positions are numbered by taking the first N-terminal amino acid M of SEQ ID NO: 2 as 1. Of lanes 3 to 9 for N terminal truncation (upper, left) and lanes 4 to 10 for C terminal truncation (upper, right), lanes in which signal was detected with antibody #4LD are indicated with +, while lanes with no detected signal are marked with −.

N terminal truncation

1: K(47)-Q(180)   2: K(47)-D(159)   10: K(47)-E(140)
+3: K(47)----------P(155)
+4: K(47)------D(150)
+5: K(47)-----A(149)
+6: K(47)----I(148)
+7: K(47)---R(147)
−8: K(47)--V(146)
−9: K(47)-S(145)

C terminal truncation

```
 1: M(96)-Q(180)        2: L(116)-Q(180)    3: Q(128)-Q(180)
 +4:        S(131)-Q(180)
 +5:        A(132)--Q(180)
 +6:        E(133)---Q(180)
 -7:        V(134)----Q(180)
 -8:        E(135)-----Q(180)
 -9:        R(136)------Q(180)
-10:        L(137)-------Q(180)
```

As clearly seen from FIG. 6, binding of antibody 4LD was detected in lane 7 for N terminal truncation K(47)---R(147), while the binding was undetectable in lane 8 for N terminal truncation K(47)--V(146). This demonstrates that R at position 147 is essential for the antigen recognition by antibody 4LD. On the other hand, the result on the C terminal truncation (upper, right panel in FIG. 6) showed that antibody 4LD bound to E(133)---Q(180) in lane 6 while the binding to V(134)----Q(180) was undetectable. This indicates that E at position 133 is essential for the antigen recognition by antibody 4LD. The epitope recognized by 4LD was revealed to be the 15 amino acids of EVERLRRENQVLSVR (SEQ ID NO: 37). The amino acid sequence of SEQ ID NO: 37 corresponds to the region from positions 133 to 147 in the full-length amino acid sequence of BST2D (SEQ ID NO: 2). As shown in FIG. 1, this epitope was found to be constituted by a human BST2D-specific amino acid sequence.

Example 7

In Vivo Drug Efficacy Test (1) Cell Lines

The cell lines used were human myeloma-derived cell line RPMI8226 (ATCC) and human B cell line ARH77 (ATCC). The cells were passaged and maintained in RPMI1640 (SIGMA) supplemented with 10% FBS (BIONET).

(2) Preparation of Mouse Model Grafted with Human Cancer Cell Line RPMI8226

Cells were prepared at $5\times10^7$ cells/ml using the cell passage medium. On the day before cell transplantation, 100 μl of an anti-asialo GM 1 antibody (Wako Pure Chemical Industries; one vial was dissolved in 5 ml) was administered into the peritoneal cavities of SCID mice (male, five weeks old) (CLEA Japan Inc.). 100 μl of the cell suspension ($5\times10^6$ cells/head) was transplanted subcutaneously at an abdominal site into the mice. The tumor volume was calculated according to the formula shown below, and the model was approved when the tumor volume reached 140 to 240 mm³.

(Tumor volume)=(major axis)×(minor axis)×(minor axis)/2

The mice were grouped based on the tumor volume.

(3) Preparation of Mouse Model Grafted with Human Cancer Cell Line ARH77

Cells were prepared at $2.5\times10^7$ cells/ml using the cell passage medium. On the day before cell transplantation, 100 μl of an anti-asialo GM1 antibody (Wako Pure Chemical Industries; one vial was dissolved in 5 ml) was administered into the peritoneal cavities of SCID mice (male, five weeks old) (CLEA Japan Inc.). 200 μl of the cell suspension ($5\times10^6$ cells/head) was transplanted via the caudal vein into the mice. Ten days after tumor transplantation, the levels of serum human IgG (M protein) produced by ARH77 cells in the mice were determined by ELISA (see the section "Serum M protein assay"). The model was established based on the detection of M protein. The mice were grouped based on the serum M protein level.

(4) Serum M Protein Assay

Blood was collected from the dorsal metatarsal vein. After separation of sera, the M protein levels in mouse sera were determined by sandwich ELISA using an anti-human IgG antibody. Specifically, 96-well plates (Nunc) immobilized with an anti-human IgG antibody (Biosource) were blocked with dilution buffer (D.B.), and then the serum samples appropriately diluted using the dilution buffer were added thereto. Composition of the dilution buffer is shown below.

Dilution Buffer:
50 mmol/l Tris-HCl buffer (pH 8.1) containing:
1 mmol/L $MgCl_2$,
150 mmol/L NaCl,
0.02 w/v % $NaN_3$,
0.05 vol (%) Tween20, and
1 w/v % bovine serum albumin (BSA).

Furthermore, as a standard for antibody concentration determination, human IgG (ICN/cappel) was diluted in eleven serial two-fold dilutions beginning at 1000 ng/ml. The standard was also added to the plates. After reaction with an alkaline phosphatase-labeled anti-human IgG antibody (Biosource), color development was carried out using Sigma 104 (Sigma-Aldrich) as the substrate, and the resulting absorbance at 405 nm was determined using an absorbance reader (reference wavelength: 635 nm). Human IgG (M protein) levels in the samples were calculated based on the calibration curve using standard human IgG. The detection limit in the ELISA was assumed to be 1 ng/ml based on the calibration curve.

(5) Preparation of Antibody to be Administered

On the day of administration, antibody 4LD was prepared using PBS(−) sterilized by filtration at 0.5 mg/ml (group administered at 5 mg/kg); 0.15 mg/ml (group administered at 1.5 mg/kg), 0.1 mg/ml (group administered at 1 mg/kg), and 0.05 mg/ml (group administered at 0.5 mg/kg), and used for administration.

(6) Antibody Administration

The samples prepared as described above in (5) were administered to the RPMI8226 cell-grafted model mice prepared as described in (2). The samples were given at 10 ml/kg (doses: 5, 1.5, and 0.5 mg/kg) via the caudal vein twice a week for three weeks starting from 27 days after transplantation. As a negative control, PBS(−) (vehicle) was administered at 10 ml/kg via the caudal vein twice a week for three weeks by the same procedure. Each group included six mice. The samples prepared as described above in (5) were administered to the ARH77 cell-grafted model mice prepared as described in (3). The samples were administered at 10 ml/kg (doses: 5, 0.5, and 0.05 mg/kg) via the caudal vein once a week for three weeks starting from 10 days after transplantation. As a negative control, PBS(−) (vehicle) was administered at 10 ml/kg via the caudal vein once a week for three weeks by the same procedure. Each group included five mice.

(7) Assessment of Antitumor Effect

Figure 7:
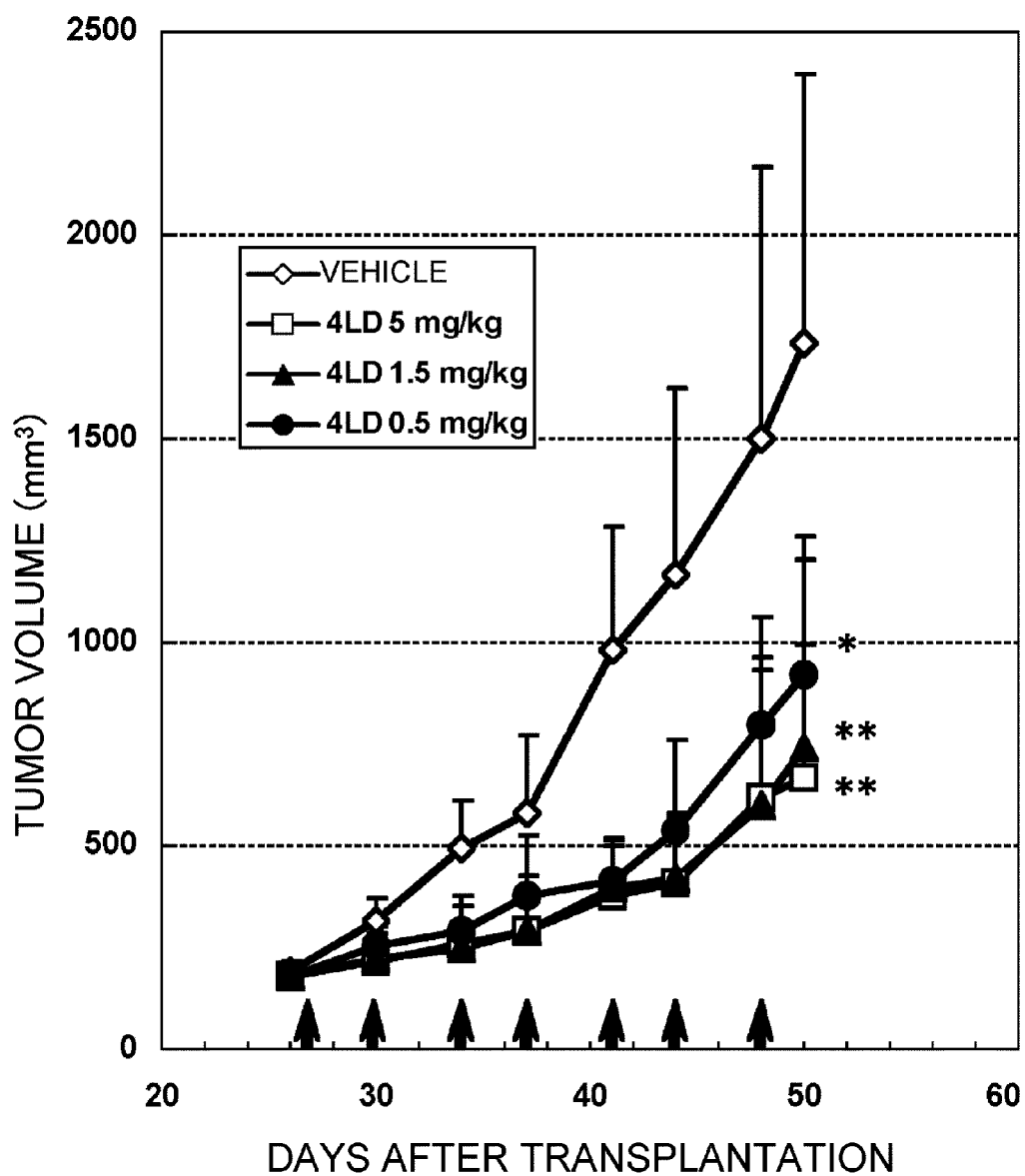
FIG. 7 presents a graph showing tumor volume changes upon administration of 4LD in model mice grafted with cells of the RPMI8226 line. Arrows indicate antibody administration. Statistical analysis was carried out by Dunnett's multiple comparison test using the tumor volume determined on the last day of measurement. **: $P<0.005$, *: $P<0.05$
Figure 8:
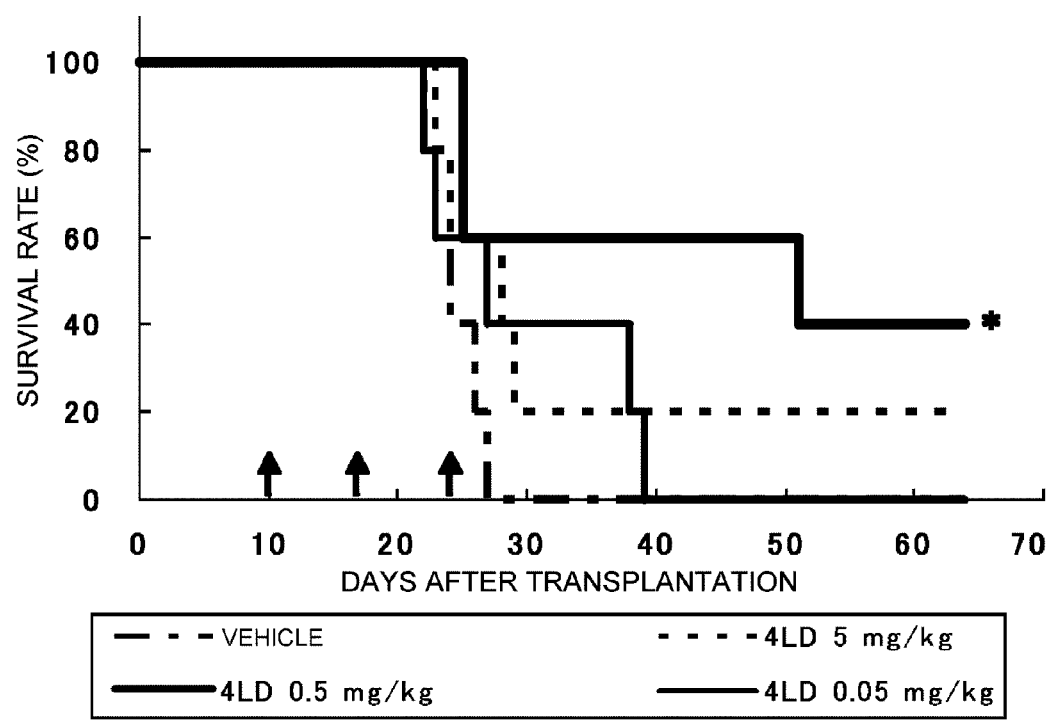
FIG. 8 presents a graph showing the survival period of 4LD-administered model mice grafted with cells of ARH77 line. Statistical analysis was carried out by Kaplan-Meier method logrank test. *:$P<0.05$

The antitumor effect of antibody 4LD in RPMI8226 cell-grafted model mice was assessed based on the time course of tumor volume change (FIG. 7). The result showed that the tumor growth was suppressed in the group administered with antibody 4LD as compared to the vehicle-administered group. The antitumor effect in ARH77 cell-grafted model mice was assessed based on the survival period (FIG. 8). The result showed that the survival period was prolonged in the group administered with antibody 4LD as compared to the vehicle-administered group.

These results demonstrate that antibody 4LD has antitumor effect on model mice transplanted with human myeloma cells.

INDUSTRIAL APPLICABILITY

The present invention provides antibodies that specifically recognize BST2D among various splicing variants of human BST2 antigen. The anti-BST2 antibodies of the present invention, which are more specific to BST2D than the conventional anti-HM1.24 antibodies, can be used in treating or diagnosing BST2D-expressing tissues and cells such as myeloma. For example, when used to treat myeloma, the antibodies of the present invention enable maintenance at high levels in the blood for a longer period than antibodies that do not immunologically distinguish BST2D from BST2H. Thus, the antibodies of the present invention can achieve therapeutic effects even at lower doses. Alternatively, the antibodies of the present invention can be used as diagnostic agents capable of specifically detecting BST2D-expressing cells such as myeloma. In particular, when used in in vivo image diagnosis for myeloma, the antibodies of the present invention which immunologically recognize other variants of BST2 molecule are useful as a diagnostic tool that gives more specific images with low background noise for lesions.

The invention claimed is:

1. An anti-human BST2 antibody that binds to human BST2D antigen but does not bind substantially to human BST2H antigen, or a fragment comprising the antigen-binding domain thereof, wherein the antibody recognizes the amino acid sequence of SEQ ID NO: 37 as an epitope.

2. An antibody that binds to the same epitope in BST2D protein as the antibody of claim 1, or a fragment comprising the antigen-binding domain thereof.

3. The antibody of claim 1 that is a monoclonal antibody, or a fragme comprising the antigen-binding domain thereof.

4. A monoclonal antibody produced by hybridoma BST2#4LD deposited under the accession number FERM BP-10964, or a fragment comprising the antigen-binding domain thereof.

5. The antibody of claim 1 whose heavy-chain and light-chain variable regions comprise as CDR1, CDR2, and CDR3 the following amino acid sequences:

heavy-chain variable region CDR1:
(SEQ ID NO: 4)
SGYYWN;

heavy-chain variable region CDR2:
(SEQ ID NO: 5)
YISYDGSNNYNPSLKNR;
and heavy-chain variable region CDR3:
(SEQ ID NO: 6)
ILGRGY;

light-chain variable region CDR1:
(SEQ ID NO: 7)
RASQSVSTSSYSYMH;

light-chain variable region CDR2:
(SEQ ID NO: 8)
YASNLES;

-continued and

```
light-chain variable region CDR3:
                                    (SEQ ID NO: 9)
QHSWEIPYT;
``` or a fragment comprising the antigen-binding domain thereof.

6. The antibody of claim 1 which comprises the heavy-chain variable region of SEQ ID NO: 11 and the light-chain variable region of SEQ ID NO: 13, or a fragment comprising the antigen-binding domain thereof.

7. An antibody of (A) or (B) below, which has an activity equivalent to that of the antibody of (A) or (B) below:
  (A) an antibody whose heavy-chain and light-chain variable regions comprise as CDR1, CDR2, and CDR3 the following amino acid sequences:

```
heavy-chain variable region CDR1:
                                    (SEQ ID NO: 4)
SGYYWN;

heavy-chain variable region CDR2:
                                    (SEQ ID NO: 5)
YISYDGSNNYNPSLKNR;
and heavy-chain variable region CDR3:
                                    (SEQ ID NO: 6)
ILGRGY;

light-chain variable region CDR1:
                                    (SEQ ID NO: 7)
RASQSVSTSSYSYMH;

light-chain variable region CDR2:
                                    (SEQ ID NO: 8)
YASNLES;
and light-chain variable region CDR3:
                                    (SEQ ID NO: 9)
QHSWEIPYT;
or
```

(B) an antibody which comprises the heavy-chain variable region of SEQ ID NO: 11 and the light-chain variable region of SEQ ID NO: 13,
  or a fragment comprising the antigen-binding domain thereof.

8. An antibody that binds to the same epitope in BST2D protein as the antibody of claim 5, or a fragment comprising the antigen-binding domain thereof.

9. The antibody of claim 5 which is a monoclonal antibody or a fragment comprising the antigen-binding domain thereof.

10. The antibody of claim 1 having CDC against a cell expressing human BST2D antigen on the cell surface, or a fragment comprising the antigen-binding domain thereof.

11. The antibody of claim 1 having ADCC against a cell expressing human BST2D antigen on the cell surface, or a fragment comprising the antigen-binding domain thereof.

12. A hybridoma that produces the antibody of claim 3.

13. The hybridoma BST2#4LD deposited under the accession number FERM BP-10964.

14. A method of antibody production comprising the steps of culturing the hybridoma of claim 13 and collecting the antibody from the culture.

15. A method for producing an anti-human BST2D specific antibody, which comprises the steps of:
  (1) contacting an anti-human BST2D antibody with either or both of human BST2H and human BST2HS; and
  (2) collecting, as an anti-human BST2D specific antibody, an anti-human BST2D antibody having either or both of the reaction specificities of:
    (i) not binding to human BST2H; and
    (ii) not binding to human BST2HS.

16. A therapeutic agent, which comprises as an active ingredient the antibody of claim 1 or a fragment comprising the antigen-binding domain thereof.

17. A diagnostic agent, which comprises the antibody of claim 1 or a fragment comprising the antigen-binding domain thereof.

18. An antibody comprising the heavy-chain variable region of SEQ ID NO: 11 and the light-chain variable region of SEQ ID NO: 13 with a substitution of 10 or less amino acids except in CDRs, wherein the antibody has an activity equivalent to that of an antibody comprising the heavy-chain variable region of SEQ ID NO: 11 and the light-chain variable region of SEQ ID NO: 13, or a fragment comprising the antigen-binding domain thereof.

19. An antibody comprising the heavy-chain variable region of SEQ ID NO: 11 and the light-chain variable region of SEQ ID NO: 13 with a substitution of 5 amino acids or less except in CDRs, wherein the antibody has an activity equivalent to that of an antibody comprising the heavy-chain variable region of SEQ ID NO: 11 and the light-chain variable region of SEQ ID NO: 13, or a fragment comprising the antigen-binding domain thereof.

* * * * *

UNITED STATES PATENT AND TRADEMARK OFFICE
CERTIFICATE OF CORRECTION

PATENT NO. : 8,529,896 B2  
APPLICATION NO. : 12/738285  
DATED : September 10, 2013  
INVENTOR(S) : Yumiko Kamogawa et al.

Page 1 of 1

It is certified that error appears in the above-identified patent and that said Letters Patent is hereby corrected as shown below:

In the Claims

Column 63, line 58, in claim 3, replace "fragme" with --fragment--.

Signed and Sealed this  
Seventeenth Day of December, 2013

Margaret A. Focarino  
*Commissioner for Patents of the United States Patent and Trademark Office*